United States Patent
Matsuzaki et al.

(10) Patent No.: US 7,151,195 B2
(45) Date of Patent: Dec. 19, 2006

(54) PHTHALAMIDE DERIVATIVE, AGRICULTURAL OR HORTICULTURAL INSECTICIDE, AND METHOD OF USE THEREOF

(75) Inventors: Yoshihiro Matsuzaki, Osaka (JP); Masayuki Morimoto, Osaka (JP); Shinsuke Fujioka, Osaka (JP); Masanori Tohnishi, Osaka (JP)

(73) Assignee: Bayer CropScience LP, Monheim (DE)

( * ) Notice: Subject to any disclaimer, the term of this patent is extended or adjusted under 35 U.S.C. 154(b) by 0 days.

(21) Appl. No.: 10/512,917
(22) PCT Filed: May 1, 2003
(86) PCT No.: PCT/JP03/05579

§ 371 (c)(1),
(2), (4) Date: Jul. 22, 2005

(87) PCT Pub. No.: WO03/093228

PCT Pub. Date: Nov. 13, 2003

(65) Prior Publication Data

US 2006/0166830 A1    Jul. 27, 2006

(30) Foreign Application Priority Data

May 2, 2002    (JP)    ................. 2002-130965

(51) Int. Cl.
 C07C 233/00    (2006.01)
 C07C 235/00    (2006.01)
 C07C 237/00    (2006.01)
 C07C 239/00    (2006.01)

(52) U.S. Cl. ............... 564/164; 564/123; 564/161; 564/163; 564/164; 424/405

(58) Field of Classification Search ........... 564/164, 564/123, 161, 163

See application file for complete search history.

(56) References Cited

U.S. PATENT DOCUMENTS 6,603,044 B1    8/2003    Tohnishi et al. ............ 564/154

FOREIGN PATENT DOCUMENTS

| | | |
|---|---|---|
| EP | 919 542 A2 | 6/1999 |
| EP | 1 193 254 A1 | 4/2002 |
| JP | 2001-157654 | 6/2001 |
| JP | 2001-335563 | 12/2001 |
| WO | WO03011028 A1 * | 8/2002 |

* cited by examiner

Primary Examiner—Johann Richter
Assistant Examiner—David P. Stitzel
(74) Attorney, Agent, or Firm—Richard E. L. Henderson

(57) ABSTRACT

The present invention relates to a phthalamide derivative represented by the general formula (I):

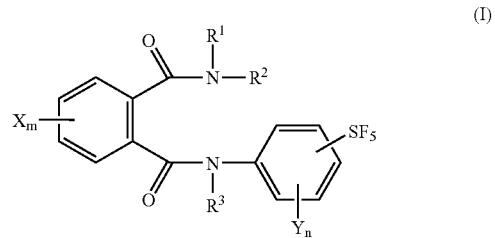

wherein $R^1$, $R^2$, $R^3$, X, Y, m, and n are as defined in the disclosure, which can be used as the active ingredient in an agricultural or horticultural insecticide that exhibits an excellent insecticidal effect even when used in a small active-ingredient amount.

4 Claims, No Drawings

PHTHALAMIDE DERIVATIVE, AGRICULTURAL OR HORTICULTURAL INSECTICIDE, AND METHOD OF USE THEREOF

RELATED APPLICATIONS

The present patent application has been filed under 35 U.S.C. 371 as a national stage application of PCT/JP03/05579, filed May 1, 2003, which was published in Japanese as International Patent Publication WO 03/093228 on Nov. 13, 2003, which is entitled to the right of priority of Japanese Patent Application 2002-130965, filed May 2, 2002.

BACKGROUND OF THE INVENTION

1. Technical Field

The present invention relates to an agrohorticultural insecticide containing a phthalamide derivative as an active ingredient, and a method of use thereof.

2. Background Art

Phthalamide derivatives similar to the present invention are known to be useful as an agrohorticultural insecticide (see, for example, Japanese Patent Application Laid-Open (KOKAI) Nos. 11-240857, 2001-131141, 2001-158764, 2001-240580, and 2001-335563). However, a phthalamide derivative having a particular substituent represented by the general formula (I) has not been disclosed or suggested.

In crop production such as agriculture and horticulture, there still exist large damages caused by insect pests or the like. Due to reasons such as appearance of insect pests resistant to existing insecticides, a novel agrohorticultural insecticide is desired to be developed. Moreover, as farmers are aged, various laborsaving application methods are desired, and an agrohorticultural insecticide having a feature suitable for such application methods is desired to be created.

DESCRIPTION OF THE INVENTION

The present inventors strenuously studied in order to develop a novel agrohorticultural insecticide, and then have accomplished the present invention by finding that a phthalamide derivative represented by the general formula (I) is a novel compound described in documents; shows an excellent insecticidal effect at a smaller dosage than those of compounds described in prior documents; and in particular, by soil treatment, shows an elevated absorption translocation action from roots and thereby has an excellent insecticidal effect.

That is, the present invention relates to a phthalamide derivative represented by the general formula (I):

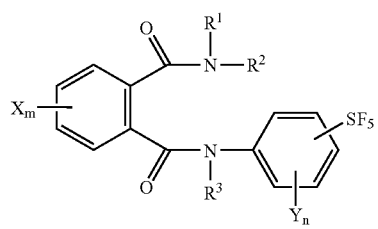

(I)

wherein $R^1$ represents hydrogen; $C_{3-6}$ cycloalkyl; halo $C_{3-6}$ cycloalkyl; phenyl; substituted phenyl having one or more substituents, which may be the same or different, and selected from halogen, $C_{1-6}$ alkyl, halo $C_{1-6}$ alkyl, $C_{1-6}$ alkoxy, halo $C_{1-6}$ alkoxy, $C_{1-6}$ alkylthio, halo $C_{1-6}$ alkylthio, $C_{1-6}$ alkylsulfinyl, halo $C_{1-6}$ alkylsulfinyl, $C_{1-6}$ alkylsulfonyl, or halo $C_{1-6}$ alkylsulfonyl; heterocyclyl; substituted heterocyclyl having one or more substituents, which may be the same or different, and selected from halogen, $C_{1-6}$ alkyl, halo $C_{1-6}$ alkyl, $C_{1-6}$ alkoxy, halo $C_{1-6}$ alkoxy, $C_{1-6}$ alkylthio, halo $C_{1-6}$ alkylthio, $C_{1-6}$ alkylsulfinyl, halo $C_{1-6}$ alkylsulfinyl, $C_{1-6}$ alkylsulfonyl, or halo $C_{1-6}$ alkylsulfonyl; or -A-(G)r in which A represents $C_{1-8}$ alkylene, $C_{3-6}$ alkenylene, or $C_{3-6}$ alkynylene; G's may be the same or different and each represents hydrogen; halogen; cyano; nitro; halo $C_{1-6}$ alkyl; $C_{3-6}$ cycloalkyl; halo $C_{3-6}$ cycloalkyl; same or different di $C_{1-6}$ alkoxyphosphoryl; same or different di $C_{1-6}$ alkoxythiophosphoryl; diphenylphosphino; diphenylphosphono; same or different $C_{1-6}$ dialkylsulfonium; phenyl; substituted phenyl having one or more substituents, which may be the same or different, and selected from halogen, $C_{1-6}$ alkyl, halo $C_{1-6}$ alkyl, $C_{1-6}$ alkoxy, halo $C_{1-6}$ alkoxy, $C_{1-6}$ alkylthio, halo $C_{1-6}$ alkylthio, $C_{1-6}$ alkylsulfinyl, halo $C_{1-6}$ alkylsulfinyl, $C_{1-6}$ alkylsulfonyl, or halo $C_{1-6}$ alkylsulfonyl; heterocyclyl; substituted heterocyclyl having one or more substituents, which may be the same or different, and selected from halogen, $C_{1-6}$ alkyl, halo $C_{1-6}$ alkyl, $C_{1-6}$ alkoxy, halo $C_{1-6}$ alkoxy, $C_{1-6}$ alkylthio, halo $C_{1-6}$ alkylthio, $C_{1-6}$ alkylsulfinyl, halo $C_{1-6}$ alkylsulfinyl, $C_{1-6}$ alkylsulfonyl, or halo $C_{1-6}$ alkylsulfonyl; -Z-$R^4$ in which Z represents —O—; —N($R^5$)— ($R^5$ represents hydrogen; $C_{1-6}$ alkylcarbonyl; halo $C_{1-6}$ alkylcarbonyl; $C_{1-6}$ alkoxycarbonyl; phenylcarbonyl; substituted phenylcarbonyl having one or more substituents, which may be the same or different, and selected from halogen, $C_{1-6}$ alkyl, halo $C_{1-6}$ alkyl, $C_{1-6}$ alkoxy, halo $C_{1-6}$ alkoxy, $C_{1-6}$ alkylthio, halo $C_{1-6}$ alkylthio, $C_{1-6}$ alkylsulfinyl, halo $C_{1-6}$ alkylsulfinyl, $C_{1-6}$ alkylsulfonyl, or halo $C_{1-6}$ alkylsulfonyl; $C_{1-6}$ alkylsulfonyl; or halo $C_{1-6}$ alkylsulfonyl); $R^4$ represents hydrogen; $C_{1-6}$ alkyl; halo $C_{1-6}$ alkyl; $C_{3-6}$ alkenyl; halo $C_{3-6}$ alkenyl; $C_{3-6}$ alkynyl; halo $C_{3-6}$ alkynyl; $C_{3-6}$ cycloalkyl; halo $C_{3-6}$ cycloalkyl; $C_{1-6}$ alkoxy $C_{1-6}$ alkyl; $C_{1-6}$ alkylthio $C_{1-6}$ alkyl; formyl; $C_{1-6}$ alkylcarbonyl; halo $C_{1-6}$ alkylcarbonyl; $C_{1-6}$ alkoxycarbonyl; mono $C_{1-6}$ alkylaminocarbonyl; same or different di $C_{1-6}$ alkylaminocarbonyl; mono $C_{1-6}$ alkylaminothiocarbonyl; same or different di $C_{1-6}$ alkylaminothiocarbonyl; same or different di $C_{1-6}$ alkoxyphosphoryl; same or different di $C_{1-6}$ alkoxythiophosphoryl; phenyl; substituted phenyl having one or more substituents, which may be the same or different, and selected from halogen, $C_{1-6}$ alkyl, halo $C_{1-6}$ alkyl, $C_{1-6}$ alkoxy, halo $C_{1-6}$ alkoxy, $C_{1-6}$ alkylthio, halo $C_{1-6}$ alkylthio, $C_{1-6}$ alkylsulfinyl, halo $C_{1-6}$ alkylsulfinyl, $C_{1-6}$ alkylsulfonyl, or halo $C_{1-6}$ alkylsulfonyl; phenyl $C_{1-4}$ alkyl; substituted phenyl $C_{1-4}$ alkyl having on a ring one or more substituents, which may be the same or different, and selected from halogen, $C_{1-6}$ alkyl, halo $C_{1-6}$ alkyl, $C_{1-6}$ alkoxy, halo $C_{1-6}$ alkoxy, $C_{1-6}$ alkylthio, halo $C_{1-6}$ alkylthio, $C_{1-6}$ alkylsulfinyl, halo $C_{1-6}$ alkylsulfinyl, $C_{1-6}$ alkylsulfonyl, or halo $C_{1-6}$ alkylsulfonyl; heterocyclyl; or substituted heterocyclyl having one or more substituents, which may be the same or different, and selected from halogen, $C_{1-6}$ alkyl, halo $C_{1-6}$ alkyl, $C_{1-6}$ alkoxy, halo $C_{1-6}$ alkoxy, $C_{1-6}$ alkylthio, halo $C_{1-6}$ alkylthio, $C_{1-6}$ alkylsulfinyl, halo $C_{1-6}$ alkylsulfinyl, $C_{1-6}$ alkylsulfonyl, or halo $C_{1-6}$ alkylsulfonyl; or —W—$R^6$ in which W represents —S—, —SO—, —$SO^2$—, —C(=O)—, —C(=S)—, or —C(=N$OR^7$)— ($R^7$ represents hydrogen; $C_{1-6}$ alkyl; halo $C_{1-6}$ alkyl; $C_{3-6}$ alkenyl; halo $C_{3-6}$ alkenyl; $C_{3-6}$ alkynyl; $C_{3-6}$ cycloalkyl; phenyl $C_{1-4}$ alkyl; or substituted phenyl $C_{1-4}$ alkyl having on a ring one or more substituents, which may be the same or different, and selected from halogen, $C_{1-6}$ alkyl, halo $C_{1-6}$ alkyl, $C_{1-6}$ alkoxy, halo $C_{1-6}$ alkoxy, $C_{1-6}$ alkylthio, halo $C_{1-6}$ alkylthio, $C_{1-6}$ alkylsulfinyl, halo $C_{1-6}$ alkylsulfinyl, $C_{1-6}$ alkylsulfonyl, or halo $C_{1-6}$ alkylsulfonyl); $R^6$ represents hydrogen; $C_{1-6}$ alkyl; halo $C_{1-6}$ alkyl; $C_{3-6}$ alkenyl; halo $C_{3-6}$ alkenyl; $C_{3-6}$ alkynyl; halo $C_{3-6}$ alkynyl; $C_{3-6}$ cycloalkyl; halo $C_{3-6}$ cycloalkyl; $C_{1-6}$ alkoxy $C_{1-6}$ alkyl; $C_{1-6}$ alkylthio $C_{1-6}$ alkyl; $C_{1-6}$ alkoxy; halo $C_{1-6}$ alkoxy; $C_{1-6}$ alkylthio; halo $C_{1-6}$ alkylthio; amino; mono $C_{1-6}$ alkylamino; same or different di $C_{1-6}$ alkylamino; $C_{1-6}$ alkoxy $C_{1-6}$ alkylamino; $C_{1-6}$ alkylthio $C_{1-6}$ alkylamino; phenyl; substituted phenyl having one or more substituents, which may be the same or different, and selected from halogen, $C_{1-6}$ alkyl, halo $C_{1-6}$ alkyl, $C_{1-6}$ alkoxy, halo $C_{1-6}$ alkoxy, $C_{1-6}$ alkylthio, halo $C_{1-6}$ alkylthio, $C_{1-6}$ alkylsulfinyl, halo $C_{1-6}$ alkylsulfinyl, $C_{1-6}$ alkylsulfonyl, or halo $C_{1-6}$ alkylsulfonyl; phenyl $C_{1-4}$ alkyl; substituted phenyl $C_{1-4}$ alkyl having on a ring one or more substituents, which may be the same or different, and selected from halogen, $C_{1-6}$ alkyl, halo $C_{1-6}$ alkyl, $C_{1-6}$ alkoxy, halo $C_{1-6}$ alkoxy, $C_{1-6}$ alkylthio, halo $C_{1-6}$ alkylthio, $C_{1-6}$ alkylsulfinyl, halo $C_{1-6}$ alkylsulfinyl, $C_{1-6}$ alkylsulfonyl, or halo $C_{1-6}$ alkylsulfonyl; phenylamino; substituted phenylamino having on a ring one or more substituents, which may be the same or different, and selected from halogen, $C_{1-6}$ alkyl, halo $C_{1-6}$ alkyl, $C_{1-6}$ alkoxy, halo $C_{1-6}$ alkoxy, $C_{1-6}$ alkylthio, halo $C_{1-6}$ alkylthio, $C_{1-6}$ alkylsulfinyl, halo $C_{1-6}$ alkylsulfinyl, $C_{1-6}$ alkylsulfonyl, or halo $C_{1-6}$ alkylsulfonyl; phenyl $C_{1-4}$ alkylamino; substituted phenyl $C_{1-4}$ alkylamino having on a ring one or more substituents, which may be the same or different, and selected from halogen, $C_{1-6}$ alkyl, halo $C_{1-6}$ alkyl, $C_{1-6}$ alkoxy, halo $C_{1-6}$ alkoxy, $C_{1-6}$ alkylthio, halo $C_{1-6}$ alkylthio, $C_{1-6}$ alkylsulfinyl, halo $C_{1-6}$ alkylsulfinyl, $C_{1-6}$ alkylsulfonyl, or halo $C_{1-6}$ alkylsulfonyl; heterocyclyl; substituted heterocyclyl having one or more substituents, which may be the same or different, and selected from halogen, $C_{1-6}$ alkyl, halo $C_{1-6}$ alkyl, $C_{1-6}$ alkoxy, halo $C_{1-6}$ alkoxy, $C_{1-6}$ alkylthio, halo $C_{1-6}$ alkylthio, $C_{1-6}$ alkylsulfinyl, halo $C_{1-6}$ alkylsulfinyl, $C_{1-6}$ alkylsulfonyl, or halo $C_{1-6}$ alkylsulfonyl; heterocyclic amino; or substituted heterocyclic amino having on a ring one or more substituents, which may be the same or different, and selected from halogen, $C_{1-6}$ alkyl, halo $C_{1-6}$ alkyl, $C_{1-6}$ alkoxy, halo $C_{1-6}$ alkoxy, $C_{1-6}$ alkylthio, halo $C_{1-6}$ alkylthio, $C_{1-6}$ alkylsulfinyl, halo $C_{1-6}$ alkylsulfinyl, $C_{1-6}$ alkylsulfonyl, or halo $C_{1-6}$ alkylsulfonyl; r represents an integer of 1 to 3; and $R^4$ or $R^6$ together with A may form a 4- to 8-membered ring that may be interrupted with 1 or 2 oxygen, sulfur, or nitrogen, which may be the same or different;

$R^2$ and $R^3$ may be the same or different and each represents hydrogen, $C_{1-6}$ alkyl, halo $C_{1-6}$ alkyl, $C_{3-6}$ alkenyl, halo $C_{3-6}$ alkenyl, $C_{3-6}$ alkynyl, halo $C_{3-6}$ alkynyl, $C_{3-6}$ cycloalkyl, halo $C_{3-6}$ cycloalkyl, $C_{1-6}$ alkoxy $C_{1-6}$ alkyl, $C_{1-6}$ alkylthio $C_{1-6}$ alkyl, formyl, $C_{1-6}$ alkylcarbonyl, halo $C_{1-6}$ alkylcarbonyl, $C_{1-6}$ alkoxycarbonyl, mono $C_{1-6}$ alkylaminocarbonyl, or same or different di $C_{1-6}$ alkylaminocarbonyl; and $R^2$ together with A, $R^1$, G, $R^4$, or $R^6$ may form a 4- to 8-membered ring that may be interrupted with 1 or 2 oxygen, sulfur, or nitrogen, which may be the same or different;

X's may be the same or different and each represents halogen, nitro, amino, mono $C_{1-6}$ alkylamino, same or different di $C_{1-6}$ alkylamino, $C_{1-6}$ alkylcarbonylamino, halo $C_{1-6}$ alkylcarbonylamino, $C_{1-6}$ alkylsulfonylamino, halo $C_{1-6}$ alkylsulfonylamino, cyano, $C_{1-6}$ alkyl, halo $C_{1-6}$ alkyl, $C_{2-6}$ alkenyl, halo $C_{2-6}$ alkenyl, $C_{2-6}$ alkynyl, halo $C_{2-6}$ alkynyl, $C_{1-6}$ alkoxy, halo $C_{1-6}$ alkoxy, $C_{1-6}$ alkylcarbonyloxy, halo $C_{1-6}$ alkylcarbonyloxy, $C_{1-6}$ alkylsulfonyloxy, halo $C_{1-6}$ alkylsulfonyloxy, $C_{1-6}$ alkylthio, halo $C_{1-6}$ alkylthio, $C_{1-6}$ alkylsulfinyl, halo $C_{1-6}$ alkylsulfinyl, $C_{1-6}$ alkylsulfonyl, or halo $C_{1-6}$ alkylsulfonyl; and two X's adjacent to each other on an aromatic ring may together form a fused ring, and the fused ring may have one or more substituents, which may be the same or different, and selected from halogen, cyano, nitro, $C_{1-6}$ alkyl, halo $C_{1-6}$ alkyl, $C_{1-6}$ alkoxy, halo $C_{1-6}$ alkoxy, $C_{1-6}$ alkylthio, halo $C_{1-6}$ alkylthio, $C_{1-6}$ alkylsulfinyl, halo $C_{1-6}$ alkylsulfinyl, $C_{1-6}$ alkylsulfonyl, or halo $C_{1-6}$ alkylsulfonyl;

m represents an integer of 0 to 2;

Y's may be the same or different and each represents halogen; nitro; cyano; $C_{1-6}$ alkyl; halo $C_{1-6}$ alkyl; cyclo $C_{3-6}$ alkyl; $C_{1-6}$ alkoxy; halo $C_{1-6}$ alkoxy; mono $C_{1-6}$ alkylamino; same or different di $C_{1-6}$ alkylamino; $C_{1-6}$ alkylthio; halo $C_{1-6}$ alkylthio; $C_{1-6}$ alkylsulfinyl; halo $C_{1-6}$ alkylsulfinyl; $C_{1-6}$ alkylsulfonyl; halo $C_{1-6}$ alkylsulfonyl; phenyl; substituted phenyl having one or more substituents, which may be the same or different, and selected from halogen, $C_{1-6}$ alkyl, halo $C_{1-6}$ alkyl, $C_{1-6}$ alkoxy, halo $C_{1-6}$ alkoxy, $C_{1-6}$ alkylthio, halo $C_{1-6}$ alkylthio, $C_{1-6}$ alkylsulfinyl, halo $C_{1-6}$ alkylsulfinyl, $C_{1-6}$ alkylsulfonyl, or halo $C_{1-6}$ alkylsulfonyl; phenyl $C_{1-4}$ alkyl; substituted phenyl $C_{1-4}$ alkyl having on a ring one or more substituents, which may be the same or different, and selected from halogen, $C_{1-6}$ alkyl, halo $C_{1-6}$ alkyl, $C_{1-6}$ alkoxy, halo $C_{1-6}$ alkoxy, $C_{1-6}$ alkylthio, halo $C_{1-6}$ alkylthio, $C_{1-6}$ alkylsulfinyl, halo $C_{1-6}$ alkylsulfinyl, $C_{1-6}$ alkylsulfonyl, or halo $C_{1-6}$ alkylsulfonyl; phenoxy; substituted phenoxy having one or more substituents, which may be the same or different, and selected from halogen, $C_{1-6}$ alkyl, halo $C_{1-6}$ alkyl, $C_{1-6}$ alkoxy, halo $C_{1-6}$ alkoxy, $C_{1-6}$ alkylthio, halo $C_{1-6}$ alkylthio, $C_{1-6}$ alkylsulfinyl, halo $C_{1-6}$ alkylsulfinyl, $C_{1-6}$ alkylsulfonyl, or halo $C_{1-6}$ alkylsulfonyl; phenylthio; substituted phenylthio having one or more substituents, which may be the same or different, and selected from halogen, $C_{1-6}$ alkyl, halo $C_{1-6}$ alkyl, $C_{1-6}$ alkoxy, halo $C_{1-6}$ alkoxy, $C_{1-6}$ alkylthio, halo $C_{1-6}$ alkylthio, $C_{1-6}$ alkylsulfinyl, halo $C_{1-6}$ alkylsulfinyl, $C_{1-6}$ alkylsulfonyl, or halo $C_{1-6}$ alkylsulfonyl; heterocyclyl; or substituted heterocyclyl having one or more substituents, which may be the same or different, and selected from halogen, cyano, nitro, $C_{1-6}$ alkyl, halo $C_{1-6}$ alkyl, $C_{1-6}$ alkoxy, halo $C_{1-6}$ alkoxy, $C_{1-6}$ alkylthio, halo $C_{1-6}$ alkylthio, $C_{1-6}$ alkylsulfinyl, halo $C_{1-6}$ alkylsulfinyl, $C_{1-6}$ alkylsulfonyl, or halo $C_{1-6}$ alkylsulfonyl; and two Y's adjacent to each other on an aromatic ring may together form a fused ring, and the fused ring may have one or more substituents, which may be the same or different, and selected from halogen, $C_{1-6}$ alkyl, halo $C_{1-6}$ alkyl, $C_{1-6}$ alkoxy, halo $C_{1-6}$ alkoxy, $C_{1-6}$ alkylthio, halo $C_{1-6}$ alkylthio, $C_{1-6}$ alkylsulfinyl, halo $C_{1-6}$ alkylsulfinyl, $C_{1-6}$ alkylsulfonyl, or halo $C_{1-6}$ alkylsulfonyl; and Y together with $R^3$ may form a 5- to 7-membered ring that may be interrupted with 1 or 2 oxygen, sulfur, or nitrogen, which may be the same or different;

n represents an integer of 0 to 3, and an agrohorticultural insecticide containing the compound as an active ingredient, as well as a method of use thereof.

The compound of the present invention shows an excellent insecticidal effect at a small dosage, and in particular, by soil treatment, shows an elevated absorption translocation action from roots.

BEST MODE FOR CARRYING OUT THE INVENTION

In the definition of the general formula (I) of a phthalamide derivative of the present invention, "halogen" refers to chlorine, bromine, iodine, or fluorine; "$C_{1-6}$ alkyl" refers to a straight-chained or branched alkyl group having 1 to 6 carbon atoms such as methyl, ethyl, normal propyl, isopropyl, normal butyl, isobutyl, secondary butyl, tertiary butyl, normal pentyl, neopentyl, and normal hexyl; "halo $C_{1-6}$ alkyl" refers to a straight-chained or branched alkyl group having 1 to 6 carbon atoms substituted by same or different, one or more halogens, for example, trifluoromethyl, difluoromethyl, perfluoroethyl, perfluoroisopropyl, chloromethyl, bromomethyl, 1-bromoethyl, and 2,3-dibromopropyl can be mentioned; "$C_{1-8}$ alkylene" refers to a straight-chained or branched alkylene group having 1 to 8 carbon atoms such as methylene, ethylene, propylene, trimethylene, dimethylmethylene, tetramethylene, isobutylene, dimethylethylene, and octamethylene; "$C_{3-6}$ alkenylene" or "$C_{3-6}$ alkynylene" also refers to a straight-chained or branched alkenylene group or alkynylene group having 3 to 6 carbon atoms; "$C_{3-6}$ cycloalkyl" refers to an alicyclic alkyl group having 3 to 6 carbon atoms such as cyclopropyl, cyclobutyl, cyclopentyl, and cyclohexyl.

"Heterocyclyl" refers to a 5- or 6-membered heterocyclyl group having one or more hetero atoms selected from oxygen, sulfur, or nitrogen, and the examples include pyridyl, pyridine N-oxide, pyrimidinyl, furyl, tetrahydrofuryl, thienyl, tetrahydrothienyl, tetrahydropyranyl, tetrahydrothiopyranyl, oxazolyl, isoxazolyl, oxadiazolyl, thiazolyl, isothiazolyl, thiadiazolyl, imidazolyl, triazolyl, and pyrazolyl; examples of "fused ring" may include naphthalene, tetrahydronaphthalene, indene, indane, quinoline, quinazoline, indole, indoline, chromane, isochromane, benzodioxane, benzodioxole, benzofuran, dihydrobenzofuran, benzothiophene, dihydrobenzothiophene, benzoxazole, benzothiazole, benzimidazole, and indazole.

The phthalamide derivative represented by the general formula (I) of the present invention sometimes contains one or more asymmetric carbon atoms or asymmetric centers in the structure, and also sometimes has two or more optical isomers and diastereomers. The present invention intends to include all of each isomer and mixtures in which such isomers are contained in any ratio. Also, the phthalamide derivative represented by the general formula (I) of the present invention sometimes contains two geometric isomers derived from a carbon-carbon double bond or a carbon-nitrogen double bond. The present invention also intends to include all of each geometric isomer and mixtures in which such isomers are contained in any ratio.

Among the phthalamide derivatives represented by the general formula (I) of the present invention, examples of preferable compounds may include a phthalamide derivative in which $R^1$ represents $C_{1-6}$ alkyl, $C_{1-6}$ alkylthio $C_{1-6}$ alkyl, $C_{1-6}$ alkylsulfinyl $C_{1-6}$ alkyl, or $C_{1-6}$ alkylsulfony $C_{1-6}$ alkyl; $R^2$ and $R^3$ represent hydrogen; X represents halogen; m represents 1; Y represents halogen or $C_{1-6}$ alkyl; n represents an integer of 0 to 2.

The phthalamide derivative represented by the general formula (I) of the present invention can be produced by, for example, the scheme shown below from an aniline derivative represented by the general formula (II) that can be produced by the schemes disclosed in UK Patent No. 2276379, WO94/21606, or the like, but also can be produced by the schemes disclosed in Japanese Patent Laid-Open Nos. 11-240857 and 2001-131141.

Scheme

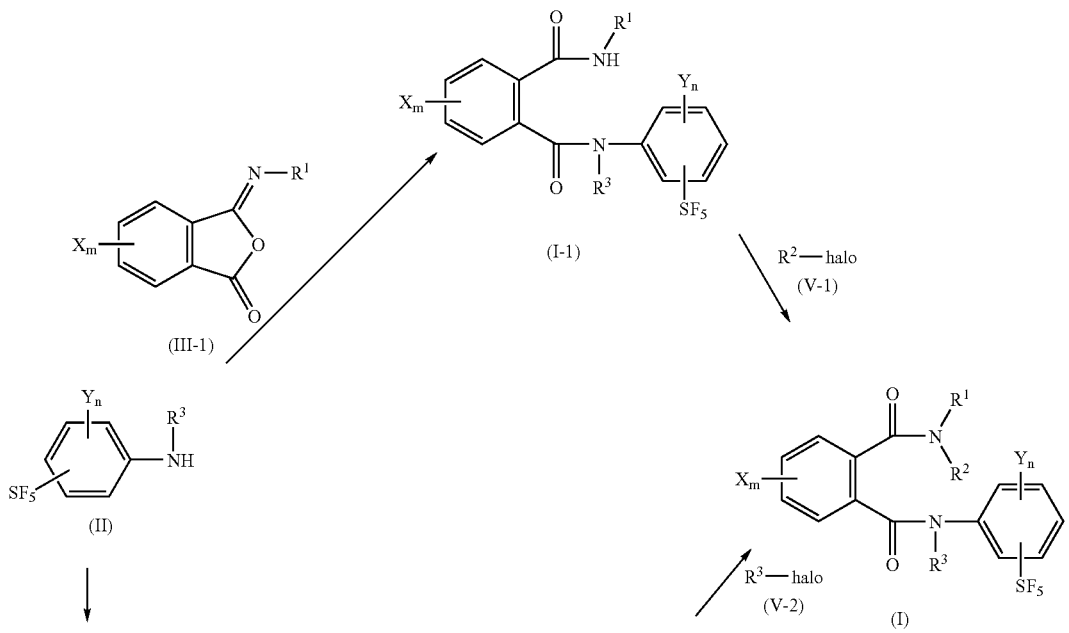

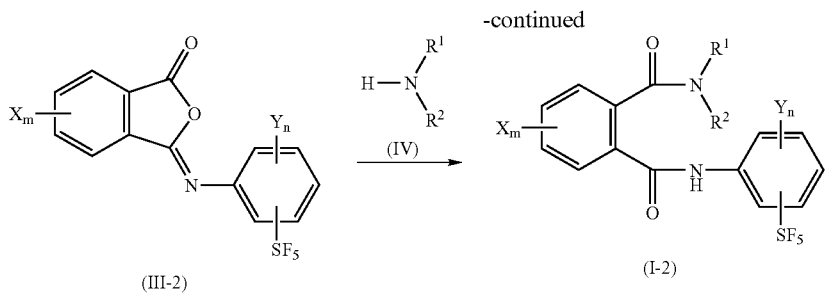

wherein each of $R^1$, $R^2$, $R^3$, X, Y, m, and n has the same meaning as described above; and "halo" represents halogen.

The phthalamide derivative represented by the general formula (I-1) can be produced by reacting the aniline derivative represented by the general formula (II) with the phthalisoimide derivative represented by the general formula (III-1) that can be produced by the scheme disclosed in Japanese Patent Laid-Open Nos. 11-240857 and 2001-131141 or the like in the presence or absence of an acid or base in an inert solvent.

The phthalamide derivative represented by the general formula (I-2) can be produced by producing the phthalisoimide derivative represented by the general formula (III-2) from the aniline derivative represented by the general formula (II) by the scheme disclosed in Japanese Patent Laid-Open Nos. 11-240857 and 2001-131141 or the like, and then reacting the phthalisoimide derivative with the amines represented by the general formula (IV) in the presence or absence of an acid or base in an inert solvent.

The phthalamide derivative represented by the general formula (I) can be produced by reacting the phthalamide derivative represented by the general formula (I-1) or (I-2) with the halides represented by the general formula (V-1) or (V-2) in the presence of a non-hydrogen halide agent and an inert solvent.

In the definition of $R^1$ of the general formula (I), when $R^1$ represents -A-(G)r, and G represents —W—$R^6$, the compound in which W represents —SO— or —$SO_2$— can be produced by subjecting the compound in which W represents —S— to an oxidative reaction, for example, using an oxidizing agent such as m-chloroperbenzoic acid and hydrogen peroxide in an ordinary manner.

1-1. General Formula (II)→General Formula (I-1) or General Formula (III-2)→General Formula (I-2)

This reaction can produce the intended product in accordance with the method described in J. Med. Chem., 10, 982 (1967). This reaction can be carried out, if required, in the presence of a catalytic amount to an excess amount of an acid or base.

Examples of acids that can be used in this reaction include organic acids such as acetic acid and trifluoroacetic acid, and inorganic acids such as hydrochloric acid and sulfuric acid. The use amount may be properly selected in the range of from a catalytic amount to an excess mole with respect to the phthalisoimide derivative represented by the general formula (III-1) or (III-2). Examples of bases include organic bases such as triethylamine and pyridine; and inorganic bases such as potassium carbonate, sodium hydrogen carbonate, sodium carbonate, and sodium hydroxide. The use amount may be properly selected in the range of from a catalytic amount to an excess mole with respect to the phthalisoimide derivative represented by the general formula (III-1) or (III-2).

The reaction temperature can be from 0° C. to the boiling point of the inert solvent to be used. The reaction time is not constant depending on the reaction scale, the reaction temperature, or the like, but within the range of several minutes to 48 hours. After completing the reaction, the intended product may be isolated from a reaction system containing the intended product in an ordinary manner, and if required, purification by recrystallization, column chromatography, or the like can be performed to produce the intended product.

1-2. General Formula (I-1)→General Formula (I) or (I-2) →General Formula (I)

Any inert solvent can be used in this reaction, as long as it does not markedly inhibit the progress of this reaction. The examples include aromatic hydrocarbons such as benzene, toluene, and xylene; halogenated aromatic hydrocarbons such as fluorobenzene, chlorobenzene, and dichlorobenzene; halogenated hydrocarbons such as methylene chloride, chloroform, and carbon tetrachloride; chained or cyclic ethers such as diethylether, dioxane, and tetrahydrofuran; esters such as ethyl acetate; amides such as dimethylformamide and dimethylacetamide; acids such as acetic acid; and inert solvents such as dimethylsulfoxide and 1,3-dimethyl-2-imidazolidinone. These inert solvents may be used alone or as a mixture thereof.

Examples of non-hydrogen halide agents include organic bases such as triethylamine and pyridine; and inorganic bases such as potassium carbonate, sodium hydrogen carbonate, sodium carbonate, and sodium hydroxide. This reaction is an equimolar reaction, and therefore an equimolar amount of each reaction agent may be used, but any of reaction agents can be used in excess.

The reaction temperature can be from room temperature to the reflux temperature of the inert solvent to be used. The reaction time is not constant depending on the reaction scale, the reaction temperature, or the like, but may be properly selected in the range of several minutes to 48 hours.

After completing the reaction, the intended product may be isolated from a reaction system containing the intended product in an ordinary manner, and if required, purification by recrystallization, column chromatography, or the like can be performed to produce the intended product.

Typical compounds of phthalamides represented by the general formula (I) are shown in Tables 1 to 3 below, but the present invention is not limited thereto.

In the tables, "n-" refers to normal, "s-" refers to secondary, "t-" refers to tertiary, "c-" refers to cyclo, "Ph" refers to phenyl, "Pyr" refers to pyridyl, and "C(*)" refers to asymmetric carbon.

TABLE 1

General formula (I-3)

(I-3)

[Structure: phthalamide with $X_m$ on one benzene ring (positions 3,4,5,6) with C(=O)NR$^1$R$^2$ and C(=O)NR$^3$-aryl where aryl has $Y_n$ substituents (positions 2,3,5,6) and SF$_5$ at position 4]

($R^2 = R^3 = H$)

| No. | R1 | Xm | Yn | Melting point (° C.) |
|---|---|---|---|---|
| 1-1 | CH$_3$ | 3-I | 2-CH$_3$ | |
| 1-2 | C$_2$H$_5$ | 3-I | 2-CH$_3$ | |
| 1-3 | n-C$_3$H$_7$ | 3-I | 2-CH$_3$ | |
| 1-4 | i-C$_3$H$_7$ | 3-I | 2-CH$_3$ | |
| 1-5 | c-C$_3$H$_5$ | 3-I | 2-CH$_3$ | |
| 1-6 | n-C$_4$H$_9$ | 3-I | 2-CH$_3$ | |
| 1-7 | s-C$_4$H$_9$ | 3-I | 2-CH$_3$ | |
| 1-8 | t-C$_4$H$_9$ | 3-I | 2-CH$_3$ | |
| 1-9 | i-C$_4$H$_9$ | 3-I | 2-CH$_3$ | |
| 1-10 | n-C$_5$H$_{11}$ | 3-I | 2-CH$_3$ | |
| 1-11 | s-C$_5$H$_{11}$ | 3-I | 2-CH$_3$ | |
| 1-12 | t-C$_5$H$_{11}$ | 3-I | 2-CH$_3$ | |
| 1-13 | c-C$_5$H$_9$ | 3-I | 2-CH$_3$ | |
| 1-14 | CH$_2$CH=CH$_2$ | 3-I | 2-CH$_3$ | |
| 1-15 | CH$_2$C≡CH | 3-I | 2-CH$_3$ | |
| 1-16 | CH(CH$_3$)CH=CH$_2$ | 3-I | 2-CH$_3$ | |
| 1-17 | C(CH$_3$)$_2$CH=CH$_2$ | 3-I | 2-CH$_3$ | |
| 1-18 | CH(CH$_3$)CH=CH-Ph | 3-I | 2-CH$_3$ | |
| 1-19 | C(CH$_3$)$_2$CH=CH-2-Pyr | 3-I | 2-CH$_3$ | |
| 1-20 | CH(CH$_3$)C≡CH | 3-I | 2-CH$_3$ | |
| 1-21 | C(CH$_3$)$_2$C≡CH | 3-I | 2-CH$_3$ | |
| 1-22 | C(CH$_3$)$_2$C≡C—Ph | 3-I | 2-CH$_3$ | |
| 1-23 | C(CH$_3$)$_2$C≡C-2-Pyr | 3-I | 2-CH$_3$ | |
| 1-24 | C(CH$_3$)$_2$C≡CH | 3-I | 2-CH$_3$ | |
| 1-25 | CH(CH$_3$)CF$_3$ | 3-I | 2-CH$_3$ | |
| 1-26 | CH(CH$_3$)CH$_2$CF$_3$ | 3-I | 2-CH$_3$ | |
| 1-27 | CH(CH$_3$)CH$_2$CH$_2$F | 3-I | 2-CH$_3$ | |
| 1-28 | CH(CH$_3$)CH$_2$CH$_2$Cl | 3-I | 2-CH$_3$ | |
| 1-29 | C(CH$_3$)$_2$CH$_2$CH$_2$F | 3-I | 2-CH$_3$ | |
| 1-30 | C(CH$_3$)$_2$CH$_2$CH$_2$Cl | 3-I | 2-CH$_3$ | |
| 1-31 | CH$_2$Ph | 3-I | 2-CH$_3$ | |
| 1-32 | CH(CH$_3$)Ph | 3-I | 2-CH$_3$ | |
| 1-33 | C(CH$_3$)$_2$Ph | 3-I | 2-CH$_3$ | |
| 1-34 | CH(CH$_3$)CH$_2$Ph | 3-I | 2-CH$_3$ | |
| 1-35 | C(CH$_3$)$_2$CH$_2$Ph | 3-I | 2-CH$_3$ | |
| 1-36 | CH(CH$_3$)-2-Pyr | 3-I | 2-CH$_3$ | |
| 1-37 | CH(CH$_3$)-3-Pyr | 3-I | 2-CH$_3$ | |
| 1-38 | C(CH$_3$)$_2$-2-Pyr | 3-I | 2-CH$_3$ | |
| 1-39 | C(CH$_3$)$_2$-3-Pyr | 3-I | 2-CH$_3$ | |
| 1-40 | Ph | 3-I | 2-CH$_3$ | |
| 1-41 | (3-SCH$_3$)Ph | 3-I | 2-CH$_3$ | |
| 1-42 | (4-SCH$_3$)Ph | 3-I | 2-CH$_3$ | |
| 1-43 | (3-CH$_2$SCH$_3$)Ph | 3-I | 2-CH$_3$ | |
| 1-44 | (4-CH$_2$SCH$_3$)Ph | 3-I | 2-CH$_3$ | |
| 1-45 | (3-SO$_2$NH$_2$)Ph | 3-I | 2-CH$_3$ | |
| 1-46 | (4-SO$_2$NH$_2$)Ph | 3-I | 2-CH$_3$ | |
| 1-47 | (3-CONH$_2$)Ph | 3-I | 2-CH$_3$ | |
| 1-48 | (4-CONH$_2$)Ph | 3-I | 2-CH$_3$ | |
| 1-49 | 3-Pyr | 3-I | 2-CH$_3$ | |
| 1-50 | 3-(4-SCH$_3$)Pyr | 3-I | 2-CH$_3$ | |
| 1-51 | 3-(2-CH$_3$-4-SCH$_3$)Pyr | 3-I | 2-CH$_3$ | |
| 1-52 | i-C$_3$H$_7$ | 3-I | 2-Cl | |
| 1-53 | s-C$_4$H$_9$ | 3-I | 2-Cl | |
| 1-54 | t-C$_4$H$_9$ | 3-I | 2-Cl | |
| 1-55 | s-C$_5$H$_{11}$ | 3-I | 2-Cl | |
| 1-56 | t-C$_5$H$_{11}$ | 3-I | 2-Cl | |
| 1-57 | CH$_2$CO$_2$CH$_3$ | 3-I | 2-CH$_3$ | |
| 1-58 | CH(CH$_3$)CO$_2$CH$_3$ | 3-I | 2-CH$_3$ | |
| 1-59 | CH(CH$_3$)CO$_2$C$_2$H$_5$ | 3-I | 2-CH$_3$ | |
| 1-60 | C(CH$_3$)$_2$CO$_2$CH$_3$ | 3-I | 2-CH$_3$ | |
| 1-61 | C(CH$_3$)$_2$CO$_2$C$_2$H$_5$ | 3-I | 2-CH$_3$ | |
| 1-62 | CH(CH$_3$)CH$_2$CO$_2$CH$_3$ | 3-I | 2-CH$_3$ | |

TABLE 1-continued

General formula (I-3)

(I-3)

[Structure: phthalamide with $X_m$ on one benzene ring (positions 3,4,5,6), N-R¹ and N-R³ amide groups, connected to aniline ring bearing $Y_n$ and $SF_5$ at position 4]

($R^2 = R^3 = H$)

| No. | R1 | Xm | Yn | Melting point (° C.) |
|---|---|---|---|---|
| 1-63 | $CH(CH_3)CH_2CO_2C_2H_5$ | 3-I | 2-$CH_3$ | |
| 1-64 | $C(CH_3)_2CH_2CO_2CH_3$ | 3-I | 2-$CH_3$ | |
| 1-65 | $C(CH_3)_2CH_2CO_2C_2H_5$ | 3-I | 2-$CH_3$ | |
| 1-66 | $CH(CH_3)(CH_2)_2CO_2CH_3$ | 3-I | 2-$CH_3$ | |
| 1-67 | $CH(CH_3)(CH_2)_2CO_2C_2H_5$ | 3-I | 2-$CH_3$ | |
| 1-68 | $C(CH_3)_2(CH_2)_2CO_2CH_3$ | 3-I | 2-$CH_3$ | |
| 1-69 | $C(CH_3)_2(CH_2)_2CO_2C_2H_5$ | 3-I | 2-$CH_3$ | |
| 1-70 | $CH(CH_3)CH=CHCO_2CH_3$ | 3-I | 2-$CH_3$ | |
| 1-71 | $CH(CH_3)CH=CHCO_2C_2H_5$ | 3-I | 2-$CH_3$ | |
| 1-72 | $C(CH_3)_2CH=CHCO_2CH_3$ | 3-I | 2-$CH_3$ | |
| 1-73 | $C(CH_3)_2CH=CHCO_2C_2H_5$ | 3-I | 2-$CH_3$ | |
| 1-74 | $CH(CH_3)C\equiv CCO_2CH_3$ | 3-I | 2-$CH_3$ | |
| 1-75 | $CH(CH_3)C\equiv CCO_2C_2H_5$ | 3-I | 2-$CH_3$ | |
| 1-76 | $C(CH_3)_2C\equiv CCO_2CH_3$ | 3-I | 2-$CH_3$ | |
| 1-77 | $C(CH_3)_2C\equiv CCO_2C_2H_5$ | 3-I | 2-$CH_3$ | |
| 1-78 | $CH_2CN$ | 3-I | 2-$CH_3$ | |
| 1-79 | $CH(CH_3)CN$ | 3-I | 2-$CH_3$ | |
| 1-80 | $C(CH_3)_2CN$ | 3-I | 2-$CH_3$ | |
| 1-81 | $CH(CH_3)CH_2CN$ | 3-I | 2-$CH_3$ | |
| 1-82 | $C(CH_3)_2CH_2CN$ | 3-I | 2-$CH_3$ | |
| 1-83 | $CH(CH_3)CONH_2$ | 3-I | 2-$CH_3$ | |
| 1-84 | $C(CH_3)_2CONH_2$ | 3-I | 2-$CH_3$ | |
| 1-85 | $CH(CH_3)CONHC_2H_5$ | 3-I | 2-$CH_3$ | |
| 1-86 | $C(CH_3)_2CONHC_2H_5$ | 3-I | 2-$CH_3$ | |
| 1-87 | $CH(CH_3)CON(C_2H_5)_2$ | 3-I | 2-$CH_3$ | |
| 1-88 | $C(CH_3)_2CON(C_2H_5)_2$ | 3-I | 2-$CH_3$ | |
| 1-89 | $CH(CH_3)CH_2CONHC_2H_5$ | 3-I | 2-$CH_3$ | |
| 1-90 | $C(CH_3)_2CH_2CONHC_2H_5$ | 3-I | 2-$CH_3$ | |
| 1-91 | $CH(CH_3)CH_2CON(C_2H_5)_2$ | 3-I | 2-$CH_3$ | |
| 1-92 | $C(CH_3)_2CH_2CON(C_2H_5)_2$ | 3-I | 2-$CH_3$ | |
| 1-93 | $C(CH_3)_2(CH_2)_2CONHC_2H_5$ | 3-I | 2-$CH_3$ | |
| 1-94 | $C(CH_3)_2(CH_2)_2CON(C_2H_5)_2$ | 3-I | 2-$CH_3$ | |
| 1-95 | $CH(CH_3)CH=CHCONHC_2H_5$ | 3-I | 2-$CH_3$ | |
| 1-96 | $CH(CH_3)CH=CHCON(C_2H_5)_2$ | 3-I | 2-$CH_3$ | |
| 1-97 | $C(CH_3)_2CH=CHCONHC_2H_5$ | 3-I | 2-$CH_3$ | |
| 1-98 | $C(CH_3)_2CH=CHCON(C_2H_5)_2$ | 3-I | 2-$CH_3$ | |
| 1-99 | $CH(CH_3)C\equiv CCONHC_2H_5$ | 3-I | 2-$CH_3$ | |
| 1-100 | $CH(CH_3)C\equiv CCON(C_2H_5)_2$ | 3-I | 2-$CH_3$ | |
| 1-101 | $C(CH_3)_2C\equiv CCONHC_2H_5$ | 3-I | 2-$CH_3$ | |
| 1-102 | $C(CH_3)_2C\equiv CCON(C_2H_5)_2$ | 3-I | 2-$CH_3$ | |
| 1-103 | $CH(CH_3)CH=O$ | 3-I | 2-$CH_3$ | |
| 1-104 | $C(CH_3)_2CH=O$ | 3-I | 2-$CH_3$ | |
| 1-105 | $CH(CH_3)C(=O)CH_3$ | 3-I | 2-$CH_3$ | |
| 1-106 | $C(CH_3)_2C(=O)CH_3$ | 3-I | 2-$CH_3$ | |
| 1-107 | $CH(CH_3)CH=NOH$ | 3-I | 2-$CH_3$ | |
| 1-108 | $C(CH_3)_2CH=NOH$ | 3-I | 2-$CH_3$ | |
| 1-109 | $CH(CH_3)C(=O)CH_3$ | 3-I | 2-$CH_3$ | |
| 1-110 | $C(CH_3)_2C(=O)CH_3$ | 3-I | 2-$CH_3$ | |
| 1-111 | $CH(CH_3)CH=NOCH_3$ | 3-I | 2-$CH_3$ | |
| 1-112 | $C(CH_3)_2CH=NOCH_3$ | 3-I | 2-$CH_3$ | |
| 1-113 | $CH(CH_3)CH=NOC_2H_5$ | 3-I | 2-$CH_3$ | |
| 1-114 | $C(CH_3)_2CH=NOC_2H_5$ | 3-I | 2-$CH_3$ | |
| 1-115 | $CH(CH_3)CH_2CH=NOCH_3$ | 3-I | 2-$CH_3$ | |
| 1-116 | $C(CH_3)_2CH_2CH=NOCH_3$ | 3-I | 2-$CH_3$ | |
| 1-117 | $CH(CH_3)CH_2CH=NOC_2H_5$ | 3-I | 2-$CH_3$ | |
| 1-118 | $C(CH_3)_2CH_2CH=NOC_2H_5$ | 3-I | 2-$CH_3$ | |
| 1-119 | $CH(CH_3)CH_2CH=NOCH_2Ph$ | 3-I | 2-$CH_3$ | |
| 1-120 | $C(CH_3)_2CH_2CH=NOCH_2Ph$ | 3-I | 2-$CH_3$ | |
| 1-121 | $CH(CH_3)CH=NOCH_2CH=CH_2$ | 3-I | 2-$CH_3$ | |
| 1-122 | $C(CH_3)_2CH=NOCH_2CH=CH_2$ | 3-I | 2-$CH_3$ | |
| 1-123 | $CH(CH_3)CH=NOCH_2C\equiv CH$ | 3-I | 2-$CH_3$ | |
| 1-124 | $C(CH_3)_2CH=NOCH_2C\equiv CH$ | 3-I | 2-$CH_3$ | |

TABLE 1-continued

General formula (I-3)

(I-3)

$$\text{X}_m \underset{5\phantom{aa}6}{\overset{4\phantom{aa}3}{\bigcirc}} \begin{matrix} \text{O} & \text{R}^1 \\ \| & | \\ \text{C}-\text{N}-\text{R}^2 \\ \text{C}-\text{N} \\ \| & | \\ \text{O} & \text{R}^3 \end{matrix} \underset{6\phantom{a}\text{Y}_n\phantom{a}5}{\overset{2\phantom{aaa}3}{\bigcirc}} \text{SF}_5$$

($R^2 = R^3 = H$)

| No. | R1 | Xm | Yn | Melting point (° C.) |
|---|---|---|---|---|
| 1-125 | CH(CH$_3$)CH=NO(CH$_2$)$_2$OCH$_3$ | 3-I | 2-CH$_3$ | |
| 1-126 | C(CH$_3$)$_2$CH=NO(CH$_2$)$_2$OCH$_3$ | 3-I | 2-CH$_3$ | |
| 1-127 | CH(CH$_3$)CH=NO(CH$_2$)$_2$OC$_2$H$_5$ | 3-I | 2-CH$_3$ | |
| 1-128 | C(CH$_3$)$_2$CH=NO(CH$_2$)$_2$OC$_2$H$_5$ | 3-I | 2-CH$_3$ | |
| 1-129 | CH(CH$_3$)CH=NO(CH$_2$)$_2$SCH$_3$ | 3-I | 2-CH$_3$ | |
| 1-130 | C(CH$_3$)$_2$CH=NO(CH$_2$)$_2$SCH$_3$ | 3-I | 2-CH$_3$ | |
| 1-131 | CH(CH$_3$)CH=NOCH$_2$CO$_2$C$_2$H$_5$ | 3-I | 2-CH$_3$ | |
| 1-132 | C(CH$_3$)$_2$CH=NOCH$_2$CO$_2$C$_2$H$_5$ | 3-I | 2-CH$_3$ | |
| 1-133 | CH(CH$_3$)C(CH$_3$)=NOCH$_3$ | 3-I | 2-CH$_3$ | |
| 1-134 | C(CH$_3$)$_2$C(CH$_3$)=NOCH$_3$ | 3-I | 2-CH$_3$ | |
| 1-135 | CH(CH$_3$)C(CH$_3$)=NOC$_2$H$_5$ | 3-I | 2-CH$_3$ | |
| 1-136 | C(CH$_3$)$_2$C(CH$_3$)=NOC$_2$H$_5$ | 3-I | 2-CH$_3$ | |
| 1-137 | C(CH$_3$)$_2$CH$_2$CO$_2$C$_2$H$_5$ | 3-I | 2-Cl | |
| 1-138 | C(CH$_3$)$_2$(CH$_2$)$_2$CO$_2$C$_2$H$_5$ | 3-I | 2-Cl | |
| 1-139 | CH(CH$_3$)CH=CHCO$_2$C$_2$H$_5$ | 3-I | 2-Cl | |
| 1-140 | C(CH$_3$)$_2$CH=CHCO$_2$C$_2$H$_5$ | 3-I | 2-Cl | |
| 1-141 | C(CH$_3$)$_2$C≡CCO$_2$C$_2$H$_5$ | 3-I | 2-Cl | |
| 1-142 | C(CH$_3$)$_2$CH$_2$CN | 3-I | 2-Cl | |
| 1-143 | C(CH$_3$)$_2$CONHC$_2$H$_5$ | 3-I | 2-Cl | |
| 1-144 | C(CH$_3$)$_2$CON(C$_2$H$_5$)$_2$ | 3-I | 2-Cl | |
| 1-145 | C(CH$_3$)$_2$CH$_2$CONHC$_2$H$_5$ | 3-I | 2-Cl | |
| 1-146 | C(CH$_3$)$_2$CH$_2$CON(C$_2$H$_5$)$_2$ | 3-I | 2-Cl | |
| 1-147 | C(CH$_3$)$_2$(CH$_2$)$_2$CONHC$_2$H$_5$ | 3-I | 2-Cl | |
| 1-148 | C(CH$_3$)$_2$(CH$_2$)$_2$CON(C$_2$H$_5$)$_2$ | 3-I | 2-Cl | |
| 1-149 | C(CH$_3$)$_2$CH=CHCONHC$_2$H$_5$ | 3-I | 2-Cl | |
| 1-150 | C(CH$_3$)$_2$CH=CHCON(C$_2$H$_5$)$_2$ | 3-I | 2-Cl | |
| 1-151 | C(CH$_3$)$_2$CH=NOH | 3-I | 2-Cl | |
| 1-152 | C(CH$_3$)$_2$CH=NOCH$_3$ | 3-I | 2-Cl | |
| 1-153 | C(CH$_3$)$_2$CH=NOCH$_2$CH=CH$_2$ | 3-I | 2-Cl | |
| 1-154 | C(CH$_3$)$_2$CH=NOCH$_2$C≡CH | 3-I | 2-Cl | |
| 1-155 | C(CH$_3$)$_2$CH$_2$CH=NOH | 3-I | 2-Cl | |
| 1-156 | C(CH$_3$)$_2$CH$_2$CH=NOCH$_3$ | 3-I | 2-Cl | |
| 1-157 | (CH$_2$)$_2$OCH$_3$ | 3-I | 2-CH$_3$ | |
| 1-158 | (CH$_2$)$_3$OCH$_3$ | 3-I | 2-CH$_3$ | |
| 1-159 | (CH$_2$)$_2$OC$_2$H$_5$ | 3-I | 2-CH$_3$ | |
| 1-160 | CH(CH$_3$)CH$_2$OH | 3-I | 2-CH$_3$ | |
| 1-161 | C(CH$_3$)$_2$CH$_2$OH | 3-I | 2-CH$_3$ | |
| 1-162 | CH(CH$_3$)CH$_2$OCH$_3$ | 3-I | 2-CH$_3$ | |
| 1-163 | C(CH$_3$)$_2$CH$_2$OCH$_3$ | 3-I | 2-CH$_3$ | |
| 1-164 | CH(CH$_3$)CH$_2$OC$_2$H$_5$ | 3-I | 2-CH$_3$ | |
| 1-165 | C(CH$_3$)$_2$CH$_2$OC$_2$H$_5$ | 3-I | 2-CH$_3$ | |
| 1-166 | CH(CH$_3$)CH$_2$OCH$_2$CH=CH$_2$ | 3-I | 2-CH$_3$ | |
| 1-167 | C(CH$_3$)$_2$CH$_2$OCH$_2$CH=CH$_2$ | 3-I | 2-CH$_3$ | |
| 1-168 | CH(CH$_3$)CH$_2$OCH$_2$C≡CH | 3-I | 2-CH$_3$ | |
| 1-169 | C(CH$_3$)$_2$CH$_2$OCH$_2$C≡CH | 3-I | 2-CH$_3$ | |
| 1-170 | CH(CH$_3$)(CH$_2$)$_2$OCH$_3$ | 3-I | 2-CH$_3$ | |
| 1-171 | C(CH$_3$)$_2$(CH$_2$)$_2$OCH$_3$ | 3-I | 2-CH$_3$ | |
| 1-172 | CH(CH$_3$)(CH$_2$)$_3$OCH$_3$ | 3-I | 2-CH$_3$ | |
| 1-173 | C(CH$_3$)$_2$(CH$_2$)$_3$OCH$_3$ | 3-I | 2-CH$_3$ | |
| 1-174 | CH(CH$_3$)(CH$_2$)$_4$OCH$_3$ | 3-I | 2-CH$_3$ | |
| 1-175 | C(CH$_3$)$_2$(CH$_2$)$_4$OCH$_3$ | 3-I | 2-CH$_3$ | |
| 1-176 | CH(CH$_3$)CH$_2$OCH$_2$CF$_3$ | 3-I | 2-CH$_3$ | |
| 1-177 | C(CH$_3$)$_2$CH$_2$OCH$_2$CF$_3$ | 3-I | 2-CH$_3$ | |
| 1-178 | CH(CH$_3$)CH$_2$OCH$_2$CN | 3-I | 2-CH$_3$ | |
| 1-179 | C(CH$_3$)$_2$CH$_2$OCH$_2$CN | 3-I | 2-CH$_3$ | |
| 1-180 | CH(CH$_3$)CH$_2$OCH$_2$CO$_2$N(CH$_3$)$_2$ | 3-I | 2-Cl | |
| 1-181 | C(CH$_3$)$_2$CH$_2$OCH$_2$CO$_2$N(CH$_3$)$_2$ | 3-I | 2-Cl | |
| 1-182 | CH(CH$_3$)CH$_2$O(CH$_2$)$_2$OCH$_3$ | 3-I | 2-CH$_3$ | |
| 1-183 | C(CH$_3$)$_2$CH$_2$O(CH$_2$)$_2$OCH$_3$ | 3-I | 2-CH$_3$ | |
| 1-184 | CH(CH$_3$)CH$_2$OCH$_2$Ph | 3-I | 2-CH$_3$ | |
| 1-185 | C(CH$_3$)$_2$CH$_2$OCH$_2$Ph | 3-I | 2-CH$_3$ | |
| 1-186 | CH(CH$_3$)CH$_2$O-Ph | 3-I | 2-CH$_3$ | |

TABLE 1-continued

General formula (I-3)

(I-3)

[Structure: phthalamide with R¹ on one amide N, R² on same N; other amide has R³ and N-aryl group bearing SF₅ at 4-position and Y_n; X_m on benzene ring positions 3-6]

($R^2 = R^3 = H$)

| No. | R1 | Xm | Yn | Melting point (° C.) |
|---|---|---|---|---|
| 1-187 | C(CH$_3$)$_2$CH$_2$O-Ph | 3-I | 2-CH$_3$ | |
| 1-188 | CH(CH$_3$)CH$_2$O-2-Pyr | 3-I | 2-CH$_3$ | |
| 1-189 | C(CH$_3$)$_2$CH$_2$O-2-Pyr | 3-I | 2-CH$_3$ | |
| 1-190 | CH(CH$_3$)CH$_2$O-3-Pyr | 3-I | 2-CH$_3$ | |
| 1-191 | C(CH$_3$)$_2$CH$_2$O-3-Pyr | 3-I | 2-CH$_3$ | |
| 1-192 | CH(CH$_3$)CH$_2$OC(=O)CH$_3$ | 3-I | 2-CH$_3$ | |
| 1-193 | C(CH$_3$)$_2$CH$_2$OC(=O)CH$_3$ | 3-I | 2-CH$_3$ | |
| 1-194 | CH(CH$_3$)CH$_2$OC(=O)CF$_3$ | 3-I | 2-CH$_3$ | |
| 1-195 | C(CH$_3$)$_2$CH$_2$OC(=O)CF$_3$ | 3-I | 2-CH$_3$ | |
| 1-196 | CH(CH$_3$)CH$_2$OCO$_2$CH$_3$ | 3-I | 2-CH$_3$ | |
| 1-197 | C(CH$_3$)$_2$CH$_2$OCO$_2$CH$_3$ | 3-I | 2-CH$_3$ | |
| 1-198 | CH(CH$_3$)CH$_2$OC(=O)NHCH$_3$ | 3-I | 2-CH$_3$ | |
| 1-199 | C(CH$_3$)$_2$CH$_2$OC(=O)NHCH$_3$ | 3-I | 2-CH$_3$ | |
| 1-200 | CH(CH$_3$)CH$_2$OC(=O)NH(C$_2$H$_5$) | 3-I | 2-CH$_3$ | |
| 1-201 | C(CH$_3$)$_2$CH$_2$OC(=O)NH(C$_2$H$_5$) | 3-I | 2-CH$_3$ | |
| 1-202 | CH(CH$_3$)CH$_2$OC(=O)N(CH$_3$)$_2$ | 3-I | 2-CH$_3$ | |
| 1-203 | C(CH$_3$)$_2$CH$_2$OC(=O)N(CH$_3$)$_2$ | 3-I | 2-CH$_3$ | |
| 1-204 | CH(CH$_3$)CH$_2$OC(=O)N(C$_2$H$_5$)$_2$ | 3-I | 2-CH$_3$ | |
| 1-205 | C(CH$_3$)$_2$CH$_2$OC(=O)N(C$_2$H$_5$)$_2$ | 3-I | 2-CH$_3$ | |
| 1-206 | CH(CH$_3$)CH$_2$OC(=O)NHCH$_2$Ph | 3-I | 2-CH$_3$ | |
| 1-207 | C(CH$_3$)$_2$CH$_2$OC(=O)NHCH$_2$Ph | 3-I | 2-CH$_3$ | |
| 1-208 | C(CH$_3$)$_2$CH$_2$OCONH(CH$_2$)$_3$SCH$_3$ | 3-I | 2-CH$_3$ | |
| 1-209 | C(CH$_3$)$_2$CH$_2$OCONH(CH$_2$)$_2$OCH$_3$ | 3-I | 2-CH$_3$ | |
| 1-210 | CH(CH$_3$)CH$_2$OC(=S)NHCH$_3$ | 3-I | 2-CH$_3$ | |
| 1-211 | C(CH$_3$)CH$_2$OC(=S)NHCH$_3$ | 3-I | 2-CH$_3$ | |
| 1-212 | CH(CH$_3$)CH$_2$OC(=S)N(C$_2$H$_5$)$_2$ | 3-I | 2-CH$_3$ | |
| 1-213 | C(CH$_3$)CH$_2$OC(=S)N(C$_2$H$_5$)$_2$ | 3-I | 2-CH$_3$ | |
| 1-214 | CH(CH$_3$)CH$_2$OCONH(C$_2$H$_5$) | 3-I | 2-CH$_3$ | |
| 1-215 | CH(CH$_3$)CH$_2$OCON(CH$_3$)$_2$ | 3-I | 2-CH$_3$ | |
| 1-216 | CH(CH$_3$)CH$_2$OCON(C$_2$H$_5$)$_2$ | 3-I | 2-CH$_3$ | |
| 1-217 | CH(CH$_3$)CH$_2$OP(=O)(OCH$_3$)$_2$ | 3-I | 2-CH$_3$ | |
| 1-218 | C(CH$_3$)$_2$CH$_2$OP(=O)(OCH$_3$)$_2$ | 3-I | 2-CH$_3$ | |
| 1-219 | CH(CH$_3$)CH$_2$OP(=O)(OC$_2$H$_5$)$_2$ | 3-I | 2-CH$_3$ | |
| 1-220 | C(CH$_3$)$_2$CH$_2$OP(=O)(OC$_2$H$_5$)$_2$ | 3-I | 2-CH$_3$ | |
| 1-221 | CH(CH$_3$)CH$_2$OP(=S)(OCH$_3$)$_2$ | 3-I | 2-CH$_3$ | |
| 1-222 | C(CH$_3$)$_2$CH$_2$OP(=S)(OCH$_3$)$_2$ | 3-I | 2-CH$_3$ | |
| 1-223 | CH(CH$_3$)CH$_2$OP(=S)(OC$_2$H$_5$)$_2$ | 3-I | 2-CH$_3$ | |
| 1-224 | C(CH$_3$)$_2$CH$_2$OP(=S)(OC$_2$H$_5$)$_2$ | 3-I | 2-CH$_3$ | |
| 1-225 | CH(CH$_3$)CH$_2$OCH$_3$ | 3-I | 2-Cl | |
| 1-226 | C(CH$_3$)$_2$CH$_2$OCH$_3$ | 3-I | 2-Cl | |
| 1-227 | CH(CH$_3$)CH$_2$OC$_2$H$_5$ | 3-I | 2-Cl | |
| 1-228 | C(CH$_3$)$_2$CH$_2$OC$_2$H$_5$ | 3-I | 2-Cl | |
| 1-229 | CH(CH$_3$)(CH$_2$)$_2$OCH$_3$ | 3-I | 2-Cl | |
| 1-230 | C(CH$_3$)$_2$(CH$_2$)$_2$OCH$_3$ | 3-I | 2-Cl | |
| 1-231 | C(CH$_3$)$_2$(CH$_2$)$_3$OCH$_3$ | 3-I | 2-Cl | |
| 1-232 | C(CH$_3$)$_2$(CH$_2$)$_4$OCH$_3$ | 3-I | 2-Cl | |
| 1-233 | C(CH$_3$)$_2$CH$_2$OP(=S)(OCH$_3$)$_2$ | 3-I | 2-Cl | |
| 1-234 | CH(CH$_3$)CH$_2$OP(=S)(OC$_2$H$_5$)$_2$ | 3-I | 2-Cl | |
| 1-235 | C(CH$_3$)$_2$CH$_2$OP(=S)(OC$_2$H$_5$)$_2$ | 3-I | 2-Cl | |
| 1-236 | CH(CH$_3$)CH$_2$NHOOCH$_3$ | 3-I | 2-CH$_3$ | |
| 1-237 | C(CH$_3$)$_2$CH$_2$NHCOCH$_3$ | 3-I | 2-CH$_3$ | |
| 1-238 | CH(CH$_3$)CH$_2$N(CH$_3$)COCH$_3$ | 3-I | 2-CH$_3$ | |
| 1-239 | C(CH$_3$)$_2$CH$_2$N(CH$_3$)COCH$_3$ | 3-I | 2-CH$_3$ | |
| 1-240 | CH(CH$_3$)CH$_2$NHCOC$_2$H$_5$ | 3-I | 2-CH$_3$ | |
| 1-241 | C(CH$_3$)$_2$CH$_2$NHCOC$_2$H$_5$ | 3-I | 2-CH$_3$ | |
| 1-242 | CH(CH$_3$)CH$_2$NHCO$_2$CH$_3$ | 3-I | 2-CH$_3$ | |
| 1-243 | C(CH$_3$)$_2$CH$_2$NHCO$_2$CH$_3$ | 3-I | 2-CH$_3$ | |
| 1-244 | CH(CH$_3$)CH$_2$NHCO$_2$C$_2$H$_5$ | 3-I | 2-CH$_3$ | |
| 1-245 | C(CH$_3$)$_2$CH$_2$NHCO$_2$C$_2$H$_5$ | 3-I | 2-CH$_3$ | |
| 1-246 | CH(CH$_3$)CH$_2$NHSO$_2$CH$_3$ | 3-I | 2-CH$_3$ | |
| 1-247 | C(CH$_3$)$_2$CH$_2$NHSO$_2$CH$_3$ | 3-I | 2-CH$_3$ | |
| 1-248 | CH(CH$_3$)CH$_2$NHSO$_2$C$_2$H$_5$ | 3-I | 2-CH$_3$ | |

TABLE 1-continued

General formula (I-3)

$$\text{(I-3)}$$

(R² = R³ = H)

| No. | R1 | Xm | Yn | Melting point (° C.) |
|---|---|---|---|---|
| 1-249 | C(CH₃)₂CH₂NHSO₂C₂H₅ | 3-I | 2-CH₃ | |
| 1-250 | CH(CH₃)CH₂N(CH₃)SO₂CH₃ | 3-I | 2-CH₃ | |
| 1-251 | C(CH₃)₂CH₂N(CH₃)SO₂CH₃ | 3-I | 2-CH₃ | |
| 1-252 | CH(CH₃)CH₂NHCONHCH₃ | 3-I | 2-CH₃ | |
| 1-253 | C(CH₃)₂CH₂NHCONHCH₃ | 3-I | 2-CH₃ | |
| 1-254 | CH(CH₃)CH₂NHCON(CH₃)₂ | 3-I | 2-CH₃ | |
| 1-255 | C(CH₃)₂CH₂NHCON(CH₃)₂ | 3-I | 2-CH₃ | |
| 1-256 | CH(CH₃)CH₂N(CH₃)CON(CH₃)₂ | 3-I | 2-CH₃ | |
| 1-257 | C(CH₃)₂CH₂N(CH₃)CON(CH₃)₂ | 3-I | 2-CH₃ | |
| 1-258 | CH(CH₃)CH₂NHCON(C₂H₅)₂ | 3-I | 2-CH₃ | |
| 1-259 | C(CH₃)₂CH₂NHCON(C₂H₅)₂ | 3-I | 2-CH₃ | |
| 1-260 | CH(CH₃)CH₂NHSO₂NHCH₃ | 3-I | 2-CH₃ | |
| 1-261 | C(CH₃)₂CH₂NHSO₂NHCH₃ | 3-I | 2-CH₃ | |
| 1-262 | CH(CH₃)CH₂NHSO₂N(CH₃)₂ | 3-I | 2-CH₃ | |
| 1-263 | C(CH₃)₂CH₂NHSO₂N(CH₃)₂ | 3-I | 2-CH₃ | |
| 1-264 | CH(CH₃)CH₂NHSO₂N(C₂H₅)₂ | 3-I | 2-CH₃ | |
| 1-265 | C(CH₃)₂CH₂NHSO₂N(C₂H₅)₂ | 3-I | 2-CH₃ | |
| 1-266 | CH(CH₃)CH₂NHP(=O)(OCH₃)₂ | 3-I | 2-CH₃ | |
| 1-267 | C(CH₃)₂CH₂NHP(=O)(OCH₃)₂ | 3-I | 2-CH₃ | |
| 1-268 | CH(CH₃)CH₂N(CH₃)P(=O)(OCH₃)₂ | 3-I | 2-CH₃ | |
| 1-269 | C(CH₃)₂CH₂N(CH₃)P(=O)(OCH₃)₂ | 3-I | 2-CH₃ | |
| 1-270 | CH(CH₃)CH₂NHP(=S)(OCH₃)₂ | 3-I | 2-CH₃ | |
| 1-271 | C(CH₃)₂CH₂NHP(=S)(OCH₃)₂ | 3-I | 2-CH₃ | |
| 1-272 | CH(CH₃)CH₂NHP(=S)(OC₂H₅)₂ | 3-I | 2-CH₃ | |
| 1-273 | C(CH₃)₂CH₂NHP(=S)(OC₂H₅)₂ | 3-I | 2-CH₃ | |
| 1-274 | CH(CH₃)CH₂NHCOCH₃ | 3-I | 2-Cl | |
| 1-275 | C(CH₃)₂CH₂NHCOCH₃ | 3-I | 2-Cl | |
| 1-276 | CH(CH₃)CH₂NHCO₂C₂H₅ | 3-I | 2-Cl | |
| 1-277 | C(CH₃)₂CH₂NHCO₂C₂H₅ | 3-I | 2-Cl | |
| 1-278 | CH(CH₃)CH₂NHSO₂CH₃ | 3-I | 2-Cl | |
| 1-279 | C(CH₃)₂CH₂NHSO₂CH₃ | 3-I | 2-Cl | |
| 1-280 | CH(CH₃)CH₂NHSO₂N(CH₃)₂ | 3-I | 2-Cl | |
| 1-281 | C(CH₃)₂CH₂NHSO₂N(CH₃)₂ | 3-I | 2-Cl | |
| 1-282 | (CH₂)₂SCH₃ | 3-I | 2-CH₃ | |
| 1-283 | (CH₂)₃SCH₃ | 3-I | 2-CH₃ | |
| 1-284 | (CH₂)₂SC₂H₅ | 3-I | 2-CH₃ | |
| 1-285 | (CH₂)₂SC₃H₇-i | 3-I | 2-CH₃ | |
| 1-286 | CH(CH₃)CH₂SH | 3-I | 2-CH₃ | |
| 1-287 | CH(CH₃)CH₂SCH₃ | 3-I | 2-CH₃ | |
| 1-288 | CH(CH₃)CH₂SOCH₃ | 3-I | 2-CH₃ | |
| 1-289 | CH(CH₃)CH₂SO₂CH₃ | 3-I | 2-CH₃ | |
| 1-290 | C(*)H(CH₃)CH₂SCH₃ (S)-enantiomer | 3-I | 2-CH₃ | 180–183 |
| 1-291 | C(*)H(CH₃)CH₂SOCH₃ (S)-enantiomer | 3-I | 2-CH₃ | |
| 1-292 | C(*)H(CH₃)CH₂SO₂CH₃ (S)-enantiomer | 3-I | 2-CH₃ | 87–90 |
| 1-293 | C(*)H(CH₃)CH₂SCH₃ (R)-enantiomer | 3-I | 2-CH₃ | |
| 1-294 | C(*)H(CH₃)CH₂SOCH₃ (R)-enantiomer | 3-I | 2-CH₃ | |
| 1-295 | C(*)H(CH₃)CH₂SO₂CH₃ (R)-enantiomer | 3-I | 2-CH₃ | |
| 1-296 | C(CH₃)₂CH₂SCH₃ | 3-I | 2-CH₃ | 216–217 |
| 1-297 | C(CH₃)₂CH₂SOCH₃ | 3-I | 2-CH₃ | 85–89 |
| 1-298 | C(CH₃)₂CH₂SO₂CH₃ | 3-I | 2-CH₃ | 115–118 |
| 1-299 | CH(CH₃)CH₂SC₂H₅ | 3-I | 2-CH₃ | |
| 1-300 | CH(CH₃)CH₂SOC₂H₅ | 3-I | 2-CH₃ | |
| 1-301 | CH(CH₃)CH₂SO₂C₂H₅ | 3-I | 2-CH₃ | |
| 1-302 | C(*)H(CH₃)CH₂SC₂H₅ (S)-enantiomer | 3-I | 2-CH₃ | |
| 1-303 | C(*)H(CH₃)CH₂SOC₂H₅ | 3-I | 2-CH₃ | |

TABLE 1-continued

General formula (I-3)

$$\text{(I-3)}$$

[Structure: benzene ring with positions 3,4,5,6 bearing $X_m$ substituent, connected via two C(=O) groups to N-R^1/N-R^2 (top amide with R^1, R^2) and N-R^3 linked to a second benzene ring (positions 2,3,4,5,6) bearing $Y_n$ and $SF_5$ at position 4]

($R^2 = R^3 = H$)

| No. | R1 | Xm | Yn | Melting point (° C.) |
|---|---|---|---|---|
| | (S)-enantiomer | | | |
| 1-304 | C(*)H(CH₃)CH₂SO₂C₂H₅ | 3-I | 2-CH₃ | |
| | (S)-enantiomer | | | |
| 1-305 | C(*)H(CH₃)CH₂SC₂H₅ | 3-I | 2-CH₃ | |
| | (R)-enantiomer | | | |
| 1-306 | C(*)H(CH₃)CH₂SOC₂H₅ | 3-I | 2-CH₃ | |
| | (R)-enantiomer | | | |
| 1-307 | C(*)H(CH₃)CH₂SO₂C₂H₅ | 3-I | 2-CH₃ | |
| | (R)-enantiomer | | | |
| 1-308 | C(CH₃)₂CH₂SC₂H₅ | 3-I | 2-CH₃ | |
| 1-309 | C(CH₃)₂CH₂SOC₂H₅ | 3-I | 2-CH₃ | |
| 1-310 | C(CH₃)₂CH₂SO₂C₂H₅ | 3-I | 2-CH₃ | |
| 1-311 | CH(CH₃)CH₂SC₃H₇-n | 3-I | 2-CH₃ | |
| 1-312 | CH(CH₃)CH₂SC₃H₇-i | 3-I | 2-CH₃ | |
| 1-313 | CH(CH₃)CH₂SCH₂CH=CH₂ | 3-I | 2-CH₃ | |
| 1-314 | CH(CH₃)CH₂SCH₂C≡CH | 3-I | 2-CH₃ | |
| 1-315 | CH(CH₃)(CH₂)₂SCH₃ | 3-I | 2-CH₃ | |
| 1-316 | C(CH₃)₂(CH₂)₂SCH₃ | 3-I | 2-CH₃ | |
| 1-317 | CH(CH₃)(CH₂)₃SCH₃ | 3-I | 2-CH₃ | |
| 1-318 | C(CH₃)₂(CH₂)₃SCH₃ | 3-I | 2-CH₃ | |
| 1-319 | CH(CH₃)(CH₂)₄SCH₃ | 3-I | 2-CH₃ | |
| 1-320 | C(CH₃)₂(CH₂)₄SCH₃ | 3-I | 2-CH₃ | |
| 1-321 | CH(C₂H₅)(CH₂)₂SCH₃ | 3-I | 2-CH₃ | |
| 1-322 | CH(CH₃)CH₂SCH₂CF₃ | 3-I | 2-CH₃ | |
| 1-323 | CH(CH₃)CH₂SCH₂CN | 3-I | 2-CH₃ | |
| 1-324 | CH(CH₃)CH₂S(CH₂)₂OCH₃ | 3-I | 2-CH₃ | |
| 1-325 | CH(CH₃)CH₂S(CH₂)₂SCH₃ | 3-I | 2-CH₃ | |
| 1-326 | CH(CH₃)CH₂SCH₂CO₂N(CH₃)₂ | 3-I | 2-CH₃ | |
| 1-327 | CH(CH₃)CH₂SCH₂CO₂N(C₂H₅)₂ | 3-I | 2-CH₃ | |
| 1-328 | CH(CH₃)CH₂SCH₂Ph | 3-I | 2-CH₃ | |
| 1-329 | CH(CH₃)CH₂S-Ph | 3-I | 2-CH₃ | |
| 1-330 | C(CH₃)₂CH₂S-Ph | 3-I | 2-CH₃ | |
| 1-331 | CH(CH₃)CH₂S-2-Pyr | 3-I | 2-CH₃ | |
| 1-332 | C(CH₃)₂CH₂S-2-Pyr | 3-I | 2-CH₃ | |
| 1-333 | CH(CH₃)CH₂S-3-Pyr | 3-I | 2-CH₃ | |
| 1-334 | C(CH₃)₂CH₂S-3-Pyr | 3-I | 2-CH₃ | |
| 1-335 | CH(CH₃)CH₂S-4-Pyr | 3-I | 2-CH₃ | |
| 1-336 | C(CH₃)₂CH₂S-4-Pyr | 3-I | 2-CH₃ | |
| 1-337 | CH(Ph)CH₂SCH₃ | 3-I | 2-CH₃ | |
| 1-338 | CH(CH₃)CH₂SCOCH₃ | 3-I | 2-CH₃ | |
| 1-339 | CH(CH₃)CH₂SCONHCH₃ | 3-I | 2-CH₃ | |
| 1-340 | C(CH₃)₂CH₂SCONHCH₃ | 3-I | 2-CH₃ | |
| 1-341 | CH(CH₃)CH₂SCON(C₂H₅)₂ | 3-I | 2-CH₃ | |
| 1-342 | C(CH₃)₂CH₂SCON(C₂H₅)₂ | 3-I | 2-CH₃ | |
| 1-343 | CH(CH₃)CH₂SC(=S)NHCH₃ | 3-I | 2-CH₃ | |
| 1-344 | C(CH₃)₂CH₂SC(=S)NHCH₃ | 3-I | 2-CH₃ | |
| 1-345 | CH(CH₃)CH₂SC(=S)N(C₂H₅)₂ | 3-I | 2-CH₃ | |
| 1-346 | C(CH₃)₂CH₂SC(=S)N(C₂H₅)₂ | 3-I | 2-CH₃ | |
| 1-347 | CH(CH₃)CH₂S—SCH₃ | 3-I | 2-CH₃ | |
| 1-348 | C(CH₃)₂CH₂S—SCH₃ | 3-I | 2-CH₃ | |
| 1-349 | CH(CH₃)CH₂SO₂NH₂ | 3-I | 2-CH₃ | |
| 1-350 | C(CH₃)₂CH₂SO₂NH₂ | 3-I | 2-CH₃ | |
| 1-351 | CH(CH₃)CH₂SO₂NHCH₃ | 3-I | 2-CH₃ | |
| 1-352 | C(CH₃)₂CH₂SO₂NHCH₃ | 3-I | 2-CH₃ | |
| 1-353 | CH(CH₃)CH₂SO₂NHC₂H₅ | 3-I | 2-CH₃ | |
| 1-354 | C(CH₃)₂CH₂SO₂NHC₂H₅ | 3-I | 2-CH₃ | |
| 1-355 | CH(CH₃)CH₂SO₂N(CH₃)₂ | 3-I | 2-CH₃ | |
| 1-356 | C(CH₃)₂CH₂SO₂N(CH₃)₂ | 3-I | 2-CH₃ | |
| 1-357 | CH(CH₃)CH₂SO₂N(C₂H₅)₂ | 3-I | 2-CH₃ | |
| 1-358 | C(CH₃)₂CH₂SO₂N(C₂H₅)₂ | 3-I | 2-CH₃ | |
| 1-359 | CH(CH₃)CH₂S(=O)OCH₃ | 3-I | 2-CH₃ | |
| 1-360 | C(CH₃)₂CH₂S(=O)OCH₃ | 3-I | 2-CH₃ | |

TABLE 1-continued

General formula (I-3)

(I-3)

($R^2 = R^3 = H$)

| No. | R1 | Xm | Yn | Melting point (° C.) |
|---|---|---|---|---|
| 1-361 | $CH(CH_3)CH_2S(=O)OC_2H_5$ | 3-I | 2-$CH_3$ | |
| 1-362 | $C(CH_3)_2CH_2S(=O)OC_2H_5$ | 3-I | 2-$CH_3$ | |
| 1-363 | $CH(CH_3)CH_2S(CH_3)=N-SO_2CH_3$ | 3-I | 2-$CH_3$ | |
| 1-364 | $C(CH_3)_2CH_2S(CH_3)=N-SO_2CH_3$ | 3-I | 2-$CH_3$ | |
| 1-365 | $CH(CH_3)CH_2S(CH_3)=N-SO_2Ph$ | 3-I | 2-$CH_3$ | |
| 1-366 | $C(CH_3)_2CH_2S(CH_3)=N-SO_2Ph$ | 3-I | 2-$CH_3$ | |
| 1-367 | $CH(CH_3)CH_2S^+(CH_3)_2I^-$ | 3-I | 2-$CH_3$ | |
| 1-368 | $C(CH_3)_2CH_2S^+(CH_3)_2I^-$ | 3-I | 2-$CH_3$ | |
| 1-369 | $CH(CH_3)CH_2SCH_3$ | 3-I | 2-Cl | |
| 1-370 | $CH(CH_3)CH_2SOCH_3$ | 3-I | 2-Cl | |
| 1-371 | $CH(CH_3)CH_2SO_2CH_3$ | 3-I | 2-Cl | |
| 1-372 | $C(CH_3)_2CH_2SCH_3$ | 3-I | 2-Cl | 170–173 |
| 1-373 | $C(CH_3)_2CH_2SOCH_3$ | 3-I | 2-Cl | 83–87 |
| 1-374 | $C(CH_3)_2CH_2SO_2CH_3$ | 3-I | 2-Cl | 196–198 |
| 1-375 | $CH(CH_3)CH_2SC_2H_5$ | 3-I | 2-Cl | |
| 1-376 | $CH(CH_3)CH_2SOC_2H_5$ | 3-I | 2-Cl | |
| 1-377 | $CH(CH_3)CH_2SO_2C_2H_5$ | 3-I | 2-Cl | |
| 1-378 | $C(CH_3)_2CH_2SC_2H_5$ | 3-I | 2-Cl | |
| 1-379 | $C(CH_3)_2CH_2SOC_2H_5$ | 3-I | 2-Cl | |
| 1-380 | $C(CH_3)_2CH_2SO_2C_2H_5$ | 3-I | 2-Cl | |
| 1-381 | $CH(CH_3)(CH_2)_2SCH_3$ | 3-I | 2-Cl | |
| 1-382 | $C(CH_3)_2(CH_2)_2SCH_3$ | 3-I | 2-Cl | |
| 1-383 | $CH(CH_3)(CH_2)_3SCH_3$ | 3-I | 2-Cl | |
| 1-384 | $C(CH_3)_2(CH_2)_3SCH_3$ | 3-I | 2-Cl | |
| 1-385 | $CH(CH_3)(CH_2)_4SCH_3$ | 3-I | 2-Cl | |
| 1-386 | $C(CH_3)_2(CH_2)_4SCH_3$ | 3-I | 2-Cl | |
| 1-387 | $CH(CH_3)CH_2SO_2NH_2$ | 3-I | 2-Cl | |
| 1-388 | $CH(CH_3)CH_2SO_2NHCH_3$ | 3-I | 2-Cl | |
| 1-389 | $CH(CH_3)CH_2SO_2NHC_2H_5$ | 3-I | 2-Cl | |
| 1-390 | $CH(CH_3)CH_2SO_2N(CH_3)_2$ | 3-I | 2-Cl | |
| 1-391 | $CH(CH_3)CH_2SO_2N(C_2H_5)_2$ | 3-I | 2-Cl | |
| 1-392 | $CH(CH_3)CH_2P(=O)(OCH_3)_2$ | 3-I | 2-$CH_3$ | |
| 1-393 | $C(CH_3)_2CH_2P(=O)(OCH_3)_2$ | 3-I | 2-$CH_3$ | |
| 1-394 | $CH(CH_3)CH_2P(=O)(OC_2H_5)_2$ | 3-I | 2-$CH_3$ | |
| 1-395 | $C(CH_3)_2CH_2P(=O)(OC_2H_5)_2$ | 3-I | 2-$CH_3$ | |
| 1-396 | $C(CH_3)_2CH_2SCH_3$ | H | 2-$CH_3$ | |
| 1-397 | $C(CH_3)_2CH_2SCH_3$ | 3-F | 2-$CH_3$ | |
| 1-398 | $C(CH_3)_2CH_2SCH_3$ | 3-Cl | 2-$CH_3$ | |
| 1-399 | $C(CH_3)_2CH_2SOCH_3$ | 3-Cl | 2-$CH_3$ | |
| 1-400 | $C(CH_3)_2CH_2SO_2CH_3$ | 3-Cl | 2-$CH_3$ | |
| 1-401 | $C(CH_3)_2CH_2SCH_3$ | 3-Br | 2-$CH_3$ | |
| 1-402 | $C(CH_3)_2CH_2SOCH_3$ | 3-Br | 2-$CH_3$ | |
| 1-403 | $C(CH_3)_2CH_2SO_2CH_3$ | 3-Br | 2-$CH_3$ | |
| 1-404 | $C(CH_3)_2CH_2SCH_3$ | 3,4-$Cl_2$ | 2-$CH_3$ | |
| 1-405 | $C(CH_3)_2CH_2SCH_3$ | 4-Cl | 2-$CH_3$ | |
| 1-406 | $C(CH_3)_2CH_2SCH_3$ | 4-Br | 2-$CH_3$ | |
| 1-407 | $C(CH_3)_2CH_2SCH_3$ | 4-I | 2-$CH_3$ | |
| 1-408 | $C(CH_3)_2CH_2SCH_3$ | 4-Cl | 2-$CH_3$ | |
| 1-409 | $C(CH_3)_2CH_2SCH_3$ | 3-$CH_3$ | 2-$CH_3$ | |
| 1-410 | $C(CH_3)_2CH_2SCH_3$ | 3-$C_2H_5$ | 2-$CH_3$ | |
| 1-411 | $C(CH_3)_2CH_2SCH_3$ | 3-i-$C_3H_7$ | 2-$CH_3$ | |
| 1-412 | $C(CH_3)_2CH_2SCH_3$ | 3-$CF_3$ | 2-$CH_3$ | |
| 1-413 | $C(CH_3)_2CH_2SCH_3$ | 3-CH=$CH_2$ | 2-$CH_3$ | |
| 1-414 | $C(CH_3)_2CH_2SCH_3$ | 3-C≡CH | 2-$CH_3$ | |
| 1-415 | $C(CH_3)_2CH_2SCH_3$ | 3-C≡CC$(CH_3)_3$ | 2-$CH_3$ | |
| 1-416 | $C(CH_3)_2CH_2SCH_3$ | 3-C≡CC$F_3$ | 2-$CH_3$ | |
| 1-417 | $C(CH_3)_2CH_2SCH_3$ | 3-$NO_2$ | 2-$CH_3$ | |
| 1-418 | $C(CH_3)_2CH_2SCH_3$ | 3-$NH_2$ | 2-$CH_3$ | |
| 1-419 | $C(CH_3)_2CH_2SCH_3$ | 3-N$(CH_3)_2$ | 2-$CH_3$ | |
| 1-420 | $C(CH_3)_2CH_2SCH_3$ | 3-NHCOC$H_3$ | 2-$CH_3$ | |
| 1-421 | $C(CH_3)_2CH_2SCH_3$ | 3-NHCOC$F_3$ | 2-$CH_3$ | |
| 1-422 | $C(CH_3)_2CH_2SCH_3$ | 3-NHC$O_2CH_3$ | 2-$CH_3$ | |

TABLE 1-continued

General formula (I-3)

$$(I-3)$$

(R² = R³ = H)

| No. | R1 | Xm | Yn | Melting point (° C.) |
|---|---|---|---|---|
| 1-423 | C(CH₃)₂CH₂SCH₃ | 3-NHSO₂CH₃ | 2-CH₃ | |
| 1-424 | C(CH₃)₂CH₂SCH₃ | 3-NHSO₂CF₃ | 2-CH₃ | |
| 1-425 | C(CH₃)₂CH₂SCH₃ | 3-OCH₃ | 2-CH₃ | |
| 1-426 | C(CH₃)₂CH₂SCH₃ | 3-OCF₃ | 2-CH₃ | |
| 1-427 | C(CH₃)₂CH₂SCH₃ | 3-OCOCH₃ | 2-CH₃ | |
| 1-428 | C(CH₃)₂CH₂SCH₃ | 3-OCOCF₃ | 2-CH₃ | |
| 1-429 | C(CH₃)₂CH₂SCH₃ | 3-OCONHCH₃ | 2-CH₃ | |
| 1-430 | C(CH₃)₂CH₂SCH₃ | 3-OCON(CH₃)₂ | 2-CH₃ | |
| 1-431 | C(CH₃)₂CH₂SCH₃ | 3-SCH₃ | 2-CH₃ | |
| 1-432 | C(CH₃)₂CH₂SCH₃ | 3-SOCH₃ | 2-CH₃ | |
| 1-433 | C(CH₃)₂CH₂SCH₃ | 3-SO₂CH₃ | 2-CH₃ | |
| 1-434 | C(CH₃)₂CH₂SCH₃ | 3-SCF₃ | 2-CH₃ | |
| 1-435 | C(CH₃)₂CH₂SCH₃ | 3-SOCF₃ | 2-CH₃ | |
| 1-436 | C(CH₃)₂CH₂SCH₃ | 3-SO₂CF₃ | 2-CH₃ | |
| 1-437 | C(CH₃)₂CH₂SCH₃ | 3-OSO₂CH₃ | 2-CH₃ | |
| 1-438 | C(CH₃)₂CH₂SCH₃ | 3-OSO₂CF₃ | 2-CH₃ | |
| 1-439 | C(CH₃)₂CH₂SCH₃ | 3-CH=CHCH=CH-4 | 2-CH₃ | |
| 1-440 | C(CH₃)₂CH₂SCH₃ | 3-OCH₂O-4 | 2-CH₃ | |
| 1-441 | C(CH₃)₂CH₂SCH₃ | 3-OCF₂O-4 | 2-CH₃ | |
| 1-442 | C(CH₃)₂CH₂SCH₃ | 3-OCF₂CF₂O-4 | 2-CH₃ | |
| 1-443 | C(CH₃)₂CH₂SCH₃ | H | 2-Cl | |
| 1-444 | C(CH₃)₂CH₂SCH₃ | 3-F | 2-Cl | |
| 1-445 | C(CH₃)₂CH₂SCH₃ | 3-Cl | 2-Cl | |
| 1-446 | C(CH₃)₂CH₂SOCH₃ | 3-Cl | 2-Cl | |
| 1-447 | C(CH₃)₂CH₂SO₂CH₃ | 3-Cl | 2-Cl | |
| 1-448 | C(CH₃)₂CH₂SCH₃ | 3-Br | 2-Cl | |
| 1-449 | C(CH₃)₂CH₂SOCH₃ | 3-Br | 2-Cl | |
| 1-450 | C(CH₃)₂CH₂SO₂CH₃ | 3-Br | 2-Cl | |
| 1-451 | C(CH₃)₂CH₂SCH₃ | 3,4-Cl₂ | 2-Cl | |
| 1-452 | C(CH₃)₂CH₂SCH₃ | 3-CF₃ | 2-Cl | |
| 1-453 | C(CH₃)₂CH₂SCH₃ | 3-NO₂ | 2-Cl | |
| 1-454 | C(CH₃)₂CH₂SCH₃ | 3-OCF₃ | 2-Cl | |
| 1-455 | C(CH₃)₂CH₂SCH₃ | 3-SCF₃ | 2-Cl | |
| 1-456 | C(CH₃)₂CH₂SCH₃ | 3-OSO₂CH₃ | 2-Cl | |
| 1-457 | C(CH₃)₂CH₂SCH₃ | 3-OSO₂CF₃ | 2-Cl | |
| 1-458 | C(CH₃)₂CH₂SCH₃ | 3-I | H | 231–232 |
| 1-459 | C(CH₃)₂CH₂SCH₃ | 3-I | H | 119–122 |
| 1-460 | C(CH₃)₂CH₂SCH₃ | 3-I | H | 118–121 |
| 1-461 | C(CH₃)₂CH₂SCH₃ | 3-I | 3-CH₃ | |
| 1-462 | CH(CH₃)CH₂SCH₃ | 3-I | 2,3-(CH₃)₂ | |
| 1-463 | CH(CH₃)CH₂SCH₃ | 3-I | 2,5-(CH₃)₂ | |
| 1-464 | CH(CH₃)CH₂SCH₃ | 3-I | 2,6-(CH₃)₂ | |
| 1-465 | CH(CH₃)CH₂SCH₃ | 3-I | 2-(CH₂)₃-3 | |
| 1-466 | CH(CH₃)CH₂SCH₃ | 3-I | 2-(CH₂)₄-3 | |
| 1-467 | C(CH₃)₂CH₂SCH₃ | 3-I | 2-C₂H₅ | |
| 1-468 | C(CH₃)₂CH₂SCH₃ | 3-I | 2-n-C₃H₇ | |
| 1-469 | C(CH₃)₂CH₂SCH₃ | 3-I | 2-i-C₃H₇ | |
| 1-470 | C(CH₃)₂CH₂SCH₃ | 3-I | 2-t-C₄H₉ | |
| 1-471 | C(CH₃)₂CH₂SCH₃ | 3-I | 2-CH₂OH | |
| 1-472 | C(CH₃)₂CH₂SCH₃ | 3-I | 2-CH₂OCH₃ | |
| 1-473 | C(CH₃)₂CH₂SCH₃ | 3-I | 2-CH₂SCH₃ | |
| 1-474 | C(CH₃)₂CH₂SCH₃ | 3-I | 2-CH₂SOCH₃ | |
| 1-475 | C(CH₃)₂CH₂SCH₃ | 3-I | 2-CH₂SO₂CH₃ | |
| 1-476 | C(CH₃)₂CH₂SCH₃ | 3-I | 2-Ph | |
| 1-477 | C(CH₃)₂CH₂SCH₃ | 3-I | 2-F | |
| 1-478 | C(CH₃)₂CH₂SCH₃ | 3-I | 2-Cl-3-F | |
| 1-479 | C(CH₃)₂CH₂SCH₃ | 3-I | 2,3-Cl₂ | |
| 1-480 | C(CH₃)₂CH₂SCH₃ | 3-I | 2,5-Cl₂ | |
| 1-481 | C(CH₃)₂CH₂SCH₃ | 3-I | 2-Br | |
| 1-482 | C(CH₃)₂CH₂SCH₃ | 3-I | 2-I | |
| 1-483 | C(CH₃)₂CH₂SCH₃ | 3-I | 2-CF₃ | |
| 1-484 | C(CH₃)₂CH₂SCH₃ | 3-I | 2-CHO | |

TABLE 1-continued

General formula (I-3)

(I-3)

$(R^2 = R^3 = H)$

| No. | R1 | Xm | Yn | Melting point (° C.) |
|---|---|---|---|---|
| 1-485 | C(CH$_3$)$_2$CH$_2$SCH$_3$ | 3-I | 2-COCH$_3$ | |
| 1-486 | C(CH$_3$)$_2$CH$_2$SCH$_3$ | 3-I | 2-CN | |
| 1-487 | C(CH$_3$)$_2$CH$_2$SCH$_3$ | 3-I | 2-CF$_3$ | |
| 1-488 | C(CH$_3$)$_2$CH$_2$SCH$_3$ | 3-I | 2-OCH$_3$ | |
| 1-489 | C(CH$_3$)$_2$CH$_2$SCH$_3$ | 3-I | 2-OCF$_3$ | |
| 1-490 | CH(CH$_3$)CH$_2$SCH$_3$ | 3-I | 2-OCH$_2$O-3 | |
| 1-491 | CH(CH$_3$)CH$_2$SCH$_3$ | 3-I | 2-OCF$_2$O-3 | |
| 1-492 | C(CH$_3$)$_2$CH$_2$SCH$_3$ | 3-I | 2-SCH$_3$ | |
| 1-493 | C(CH$_3$)$_2$CH$_2$SCH$_3$ | 3-I | 2-NO$_2$ | |
| 1-494 | C(CH$_3$)$_2$CH$_2$SCH$_3$ | 3-I | 2-N(CH$_3$)$_2$ | |
| 1-495 | C(CH$_3$)$_2$CH$_2$SCH$_3$ | 3-I | 2-CH$_3$-3-F | |
| 1-496 | C(CH$_3$)$_2$CH$_2$SCH$_3$ | 3-I | 2-CH$_3$-5-F | |
| 1-497 | C(CH$_3$)$_2$CH$_2$SCH$_3$ | 3-I | 2-CH$_3$-3-Cl | |
| 1-498 | C(CH$_3$)$_2$CH$_2$SCH$_3$ | 3-I | 2-CH$_3$-5-Cl | |
| 1-499 | C(CH$_3$)$_2$CH$_2$SCH$_3$ | 3-I | 2-CH$_3$-3-OH | |
| 1-500 | C(CH$_3$)$_2$CH$_2$SCH$_3$ | 3-I | 2-CH$_3$-3-OCH$_3$ | |

TABLE 2

General formula (I-3)

(I-3)

| No. | R$^1$ | R$^2$ | R$^3$ | Xm | Yn | Melting point (° C.) |
|---|---|---|---|---|---|---|
| 2-1 | CH$_3$ | CH$_3$ | H | 3-I | 2-CH$_3$ | |
| 2-2 | C$_2$H$_5$ | CH$_3$ | H | 3-I | 2-CH$_3$ | |
| 2-3 | C$_2$H$_5$ | C$_2$H$_5$ | H | 3-I | 2-CH$_3$ | |
| 2-4 | C$_2$H$_5$ | C$_2$H$_5$ | H | 3-I | 2-Cl | |
| 2-5 | n-C$_3$H$_7$ | CH$_3$ | H | 3-I | 2-CH$_3$ | |
| 2-6 | n-C$_3$H$_7$ | C$_2$H$_5$ | H | 3-I | 2-CH$_3$ | |
| 2-7 | n-C$_3$H$_7$ | n-C$_3$H$_7$ | H | 3-I | 2-CH$_3$ | |
| 2-8 | i-C$_3$H$_7$ | CH$_3$ | H | 3-I | 2-CH$_3$ | |
| 2-9 | i-C$_3$H$_7$ | C$_2$H$_5$ | H | 3-I | 2-CH$_3$ | |
| 2-10 | i-C$_3$H$_7$ | H | CH$_3$ | 3-I | 2-CH$_3$ | |
| 2-11 | i-C$_3$H$_7$ | COCH$_3$ | CH$_3$ | 3-I | 2-CH$_3$ | |
| 2-12 | i-C$_3$H$_7$ | H | C$_2$H$_5$ | 3-I | 2-CH$_3$ | |
| 2-13 | i-C$_3$H$_7$ | CH$_3$ | CH$_3$ | 3-I | 2-CH$_3$ | |
| 2-14 | i-C$_3$H$_7$ | CH$_3$ | COCH$_3$ | 3-I | 2-CH$_3$ | |
| 2-15 | i-C$_3$H$_7$ | CH$_3$ | H | 3-I | 2-Cl | |
| 2-16 | i-C$_3$H$_7$ | H | CH$_3$ | 3-I | 2-Cl | |
| 2-17 | CH$_2$CH$_2$SCH$_3$ | CH$_3$ | H | 3-I | 2-CH$_3$ | |
| 2-18 | CH$_2$CH$_2$SCH$_3$ | C$_2$H$_5$ | H | 3-I | 2-CH$_3$ | |
| 2-19 | CH(CH$_3$)CH$_2$SCH$_3$ | H | CH$_3$ | 3-I | 2-CH$_3$ | |
| 2-20 | CH(CH$_3$)CH$_2$SOCH$_3$ | H | CH$_3$ | 3-I | 2-CH$_3$ | |
| 2-21 | CH(CH$_3$)CH$_2$SO$_2$CH$_3$ | H | CH$_3$ | 3-I | 2-CH$_3$ | |
| 2-22 | C(CH$_3$)$_2$CH$_2$SCH$_3$ | H | CH$_3$ | 3-I | H | |
| 2-23 | C(CH$_3$)$_2$CH$_2$SOCH$_3$ | H | CH$_3$ | 3-I | H | |
| 2-24 | C(CH$_3$)$_2$CH$_2$SO$_2$CH$_3$ | H | CH$_3$ | 3-I | H | |
| 2-22 | C(CH$_3$)$_2$CH$_2$SCH$_3$ | H | C$_2$H$_5$ | 3-I | H | 54–56 |

TABLE 2-continued

General formula (I-3)

(I-3)

| No. | R¹ | R² | R³ | Xm | Yn | Melting point (° C.) |
|---|---|---|---|---|---|---|
| 2-23 | C(CH$_3$)$_2$CH$_2$SOCH$_3$ | H | C$_2$H$_5$ | 3-I | H | 86–88 |
| 2-24 | C(CH$_3$)$_2$CH$_2$SO$_2$CH$_3$ | H | C$_2$H$_5$ | 3-I | H | 81–83 |
| 2-25 | C(CH$_3$)$_2$CH$_2$SCH$_3$ | H | CH$_3$ | 3-I | 2-CH$_3$ | |
| 2-26 | C(CH$_3$)$_2$CH$_2$SOCH$_3$ | H | CH$_3$ | 3-I | 2-CH$_3$ | |
| 2-27 | C(CH$_3$)$_2$CH$_2$SO$_2$CH$_3$ | H | CH$_3$ | 3-I | 2-CH$_3$ | |
| 2-28 | C(CH$_3$)$_2$CH$_2$SCH$_3$ | H | C$_2$H$_5$ | 3-I | 2-CH$_3$ | |
| 2-29 | C(CH$_3$)$_2$CH$_2$SOCH$_3$ | H | C$_2$H$_5$ | 3-I | 2-CH$_3$ | |
| 2-30 | C(CH$_3$)$_2$CH$_2$SO$_2$CH$_3$ | H | C$_2$H$_5$ | 3-I | 2-CH$_3$ | |
| 2-31 | CH(CH$_3$)CH$_2$SC$_2$H$_5$ | H | CH$_3$ | 3-I | 2-CH$_3$ | |
| 2-32 | CH(CH$_3$)CH$_2$SOC$_2$H$_5$ | H | CH$_3$ | 3-I | 2-CH$_3$ | |
| 2-33 | CH(CH$_3$)CH$_2$SO$_2$C$_2$H$_5$ | H | CH$_3$ | 3-I | 2-CH$_3$ | |
| 2-34 | CH(CH$_3$)CH$_2$SCH$_3$ | H | CH$_3$ | 3-I | 2-Cl | |
| 2-35 | CH(CH$_3$)CH$_2$SOCH$_3$ | H | CH$_3$ | 3-I | 2-Cl | |
| 2-36 | CH(CH$_3$)CH$_2$SO$_2$CH$_3$ | H | CH$_3$ | 3-I | 2-Cl | |
| 2-37 | C(CH$_3$)$_2$CH$_2$SCH$_3$ | H | CH$_3$ | 3-I | 2-Cl | |
| 2-38 | C(CH$_3$)$_2$CH$_2$SOCH$_3$ | H | CH$_3$ | 3-I | 2-Cl | |
| 2-39 | C(CH$_3$)$_2$CH$_2$SO$_2$CH$_3$ | H | CH$_3$ | 3-I | 2-Cl | |
| 2-40 | CH(CH$_3$)CH$_2$SC$_2$H$_5$ | H | CH$_3$ | 3-I | 2-Cl | |
| 2-41 | CH(CH$_3$)CH$_2$SOC$_2$H$_5$ | H | CH$_3$ | 3-I | 2-Cl | |
| 2-42 | CH(CH$_3$)CH$_2$SO$_2$C$_2$H$_5$ | H | CH$_3$ | 3-I | 2-Cl | |

TABLE 3

General formula (I-4)

(I-4)

(R² = R³ = H)

| No. | R¹ | Xm | Yn | Melting point (° C.) |
|---|---|---|---|---|
| 3-1 | i-C$_3$H$_7$ | 3-I | H | |
| 3-2 | CH(CH$_3$)CH$_2$SCH$_3$ | 3-I | H | |
| 3-3 | CH(CH$_3$)CH$_2$SOCH$_3$ | 3-I | H | |
| 3-4 | CH(CH$_3$)CH$_2$SO$_2$CH$_3$ | 3-I | H | |
| 3-5 | C(CH$_3$)$_2$CH$_2$SCH$_3$ | 3-I | H | 170–171 |
| 3-6 | C(CH$_3$)$_2$CH$_2$SOCH$_3$ | 3-I | H | 115–118 |
| 3-7 | C(CH$_3$)$_2$CH$_2$SO$_2$CH$_3$ | 3-I | H | 120–123 |
| 3-8 | CH(CH$_3$)CH$_2$SCH$_3$ | 3-I | 2-CH$_3$ | |
| 3-9 | C(CH$_3$)$_2$CH$_2$SCH$_3$ | 3-I | 2-CH$_3$ | |
| 3-10 | CH(CH$_3$)CH$_2$SCH$_3$ | 3-I | 6-CH$_3$ | |
| 3-11 | C(CH$_3$)$_2$CH$_2$SCH$_3$ | 3-I | 6-CH$_3$ | |
| 3-12 | CH(CH$_3$)CH$_2$SCH$_3$ | 3-I | 2-C$_2$H$_5$ | |
| 3-13 | C(CH$_3$)$_2$CH$_2$SCH$_3$ | 3-I | 2-C$_2$H$_5$ | |
| 3-14 | CH(CH$_3$)CH$_2$SCH$_3$ | 3-I | 6-C$_2$H$_5$ | |
| 3-15 | C(CH$_3$)$_2$CH$_2$SCH$_3$ | 3-I | 6-C$_2$H$_5$ | |
| 3-16 | C(CH$_3$)$_2$CH$_2$SCH$_3$ | 3-I | 2-CH$_2$SCH$_3$ | |
| 3-17 | C(CH$_3$)$_2$CH$_2$SCH$_3$ | 3-I | 2-CH$_2$SOCH$_3$ | |
| 3-18 | C(CH$_3$)$_2$CH$_2$SCH$_3$ | 3-I | 2-CH$_2$SO$_2$CH$_3$ | |
| 3-19 | C(CH$_3$)$_2$CH$_2$SCH$_3$ | 3-I | 6-CH$_2$SCH$_3$ | |
| 3-20 | C(CH$_3$)$_2$CH$_2$SCH$_3$ | 3-I | 6-CH$_2$SOCH$_3$ | |
| 3-21 | C(CH$_3$)$_2$CH$_2$SCH$_3$ | 3-I | 6-CH$_2$SO$_2$CH$_3$ | |
| 3-22 | C(CH$_3$)$_2$CH$_2$SCH$_3$ | 3-I | 2-F | |
| 3-23 | C(CH$_3$)$_2$CH$_2$SCH$_3$ | 3-I | 6-F | |
| 3-24 | C(CH$_3$)$_2$CH$_2$SCH$_3$ | 3-I | 2-Cl | 205 |
| 3-25 | C(CH$_3$)$_2$CH$_2$SOCH$_3$ | 3-I | 2-Cl | |
| 3-26 | C(CH$_3$)$_2$CH$_2$SO$_2$CH$_3$ | 3-I | 2-Cl | 204 |
| 3-27 | C(CH$_3$)$_2$CH$_2$SCH$_3$ | 3-I | 4-Cl | |
| 3-28 | C(CH$_3$)$_2$CH$_2$SCH$_3$ | 3-I | 6-Cl | 221 |
| 3-29 | C(CH$_3$)$_2$CH$_2$SCH$_3$ | 3-I | 2-Br | |
| 3-30 | C(CH$_3$)$_2$CH$_2$SCH$_3$ | 3-I | 4-Br | |
| 3-31 | C(CH$_3$)$_2$CH$_2$SCH$_3$ | 3-I | 6-Br | |
| 3-32 | C(CH$_3$)$_2$CH$_2$SCH$_3$ | 3-I | 2-I | |
| 3-33 | C(CH$_3$)$_2$CH$_2$SCH$_3$ | 3-I | 4-I | |
| 3-34 | C(CH$_3$)$_2$CH$_2$SCH$_3$ | 3-I | 6-I | |
| 3-35 | C(CH$_3$)$_2$CH$_2$SCH$_3$ | 3-I | 2-CN | |
| 3-36 | C(CH$_3$)$_2$CH$_2$SCH$_3$ | 3-I | 6-CN | |
| 3-37 | C(CH$_3$)$_2$CH$_2$SCH$_3$ | 3-I | 2,4-Cl$_2$ | |
| 3-38 | C(CH$_3$)$_2$CH$_2$SCH$_3$ | 3-I | 4,6-Cl$_2$ | |

TABLE 3-continued

General formula (I-4)

(I-4)

[Structure: phthalamide with $X_m$ on left benzene ring (positions 3,4,5,6), two C(=O) groups attached to N—$R^2$ (top, with $R^1$) and N—$R^3$ (bottom), connected to right phenyl ring with SF$_5$ at position 3 and $Y_n$ substituents, positions 2,4,5,6]

($R^2 = R^3 = H$)

| No.  | $R^1$            | Xm  | Yn         | Melting point (° C.) |
|------|------------------|-----|------------|----------------------|
| 3-39 | $C(CH_3)_2CH_2SCH_3$ | 3-I | 2,4-Br$_2$ |  |
| 3-40 | $C(CH_3)_2CH_2SCH_3$ | 3-I | 2-Cl-4-Br  |  |
| 3-41 | $C(CH_3)_2CH_2SCH_3$ | 3-I | 2-Cl-4-I   |  |
| 3-42 | $C(CH_3)_2CH_2SCH_3$ | 3-I | 2-CH$_3$-4-Cl |  |
| 3-43 | $C(CH_3)_2CH_2SCH_3$ | 3-I | 2-CH$_3$-4-Br |  |
| 3-44 | $C(CH_3)_2CH_2SCH_3$ | 3-I | 2-CH$_3$-4-I |  |

Followings are typical examples of the present invention, but the present invention is not limited thereto.

EXAMPLE 1

Production of $N^1$-(2-chloro-4-pentafluorosulfanylphenyl)-$N^2$-(1,1-dimethyl-2-methylthioethyl)-3-iodophthalamide (Compound No. 1-372)

750 mg (2.0 mmol) of N-(1,1-dimethyl-2-methylthioethyl)-6-iodophthalic acid isoimide was dissolved in 10 ml of acetonitrile, 510 mg (2.0 mmol) of 2-chloro-4-pentafluorosulfanylaniline and 10 mg of trifluoroacetic acid were added, and the mixture was stirred under room temperature for 2 hours. Precipitated crystals were collected by filtration and washed with a small amount of ether to obtain 1.0 g of the intended product.
Yield: 79%
Physical property: melting point 170 to 173° C.

EXAMPLE 2

Production of $N^1$-(2-chloro-4-pentafluorosulfanylphenyl)-$N^2$-(1,1-dimethyl-2-methylsulfonylethyl)-3-iodophthalamide (Compound No. 1-374)

0.63 g (1.0 mmol) of $N^1$-(2-chloro-4-pentafluorosulfanylphenyl)-$N^2$-(1,1-dimethyl-2-methylthioethyl)-3-iodophthalamide was dissolved in 10 ml of chloroform, and the mixture was cooled to 0° C. To the solution, 0.38 g (2.2 mmol) of metachloroperbenzoic acid was added. After stirring for 1 hour, the reaction mixture solution was washed with an aqueous sodium thiosulfate solution and a 10% aqueous potassium carbonate solution, dried over anhydrous magnesium sulfate, and the solvent was distilled off under a reduced pressure to obtain 0.55 g of the intended product.
Yield: 84%
Physical property: melting point 196 to 198° C.

The agrohorticultural insecticides containing a phthalamide derivative represented by the general formula (I) of the present invention as an active ingredient, are suitable for controlling various insect pests such as agrohorticultural insect pests, stored grain insect pests, sanitary insect pests, nematodes, etc., which are injurious to paddy rice, fruit trees, vegetables, other crops, flowers, ornamental plants, etc. They have a marked insecticidal effect, for example, on LEPIDOPTERA including summer fruit tortrix (*Adoxophyes orana fasciata*), smaller tea tortrix (*Adoxophyes* sp.), Manchurian fruit moth (*Grapholita inopinata*), oriental fruit moth (*Grapholita molesta*), soybean pod border (*Leguminivora glycinivorella*), mulberry leafroller (*Olethreutes mori*), tea leafroller (*Caloptilia thevivora*), *Caloptilia* sp. (*Caloptilia zachrysa*), apple leafminer (*Phyllonorycter ringoniella*), pear barkminer (*Spulerrina astaurota*), common white (*Piers rapae crucivora*), tobacco budworm (*Heliothis* sp.), codling moth (*Laspey resia pomonella*), diamondback moth (*Plutella xylostella*), apple fruit moth (*Argyresthia conjugella*), peach fruit moth (*Carposina niponensis*), rice stem borer (*Chilo suppressalis*), rice leafroller (*Cnaphalocrocis medinalis*), tobacco moth (*Ephestia elutelia*), mulberry pyralid (*Glyphodes pyloalis*), yellow rice borer (*Scirpophaga incertulas*), rice skipper (*Parnara guttata*), rice armyworm (*Pseudaletia separata*), pink borer (*SesamIa inferens*), common cutworm (*Spodoptera litura*), beet armyworm (*Spodoptera egigua*), etc.; HEMIPTERA including aster leafhopper (*Macrosteles fascifrons*), green rice leafhopper (*Nephotettix cincticepts*), brown rice planthopper (*Nilaparvata lugens*), whitebacked rice planthopper (*Sogatella furcifera*), citrus psylla (*Diaphorina citri*), grape whitefly (*Aleurolobus taonabae*), sweetpotato whitefly (*Bemisia tabaci*), greenhouse whitefly (*Trialeurodes vaporariorum*), turnup aphid (*Lipaphis erysimi*), green peach aphid (*Myzus persicae*), Indian wax scale (*Ceroplastes ceriferus*), cottony citrus scale (*Pulvinaria aurantii*), camphor scale (*Pseudaonidia duplex*), san Jose scale (*Comstockaspis perniciosa*), arrowhead scale (*Unaspis yanonensis*), etc.; TYLENCHIDA including root-lesion nematode (*Pratylenchus* sp.), soybean beetle (*Anomala rufocuprea*), Japanese beetle (*Popilla japonica*), tobacco beetle (*Lasioderma serricorne*), powderpost beetle (*Lyctus brunneus*), twenty-eight-spotted ladybird (*Epilachna vigintiotopunctata*), azuki bean weevil (*Callosobruchus chinensis*), vegetable weevil (*Listroderes costirostris*), maize weevil (*Sitophilus zeamais*), boll weevil (*Anthonomus grandis grandis*), rice water weevil (*Lissorhoptrus oryzophilus*), cucurbit leaf beetle (*Aulacophora femoralis*), rice leaf beetle (*Oulema oryzae*), striped flea beetle (*Phyllotreta striolata*), pine shoot beetle (*Tomicus piniperda*), Colorado potato beetle (*Leptinotarsa decemlineata*), Mexican bean beetle (*Epilachna varivestis*), corn rootworm (*Diabrotica* sp.), etc. DIPTERA including Coquillet melon fly (*Dacus(Zeugodacus) cucurbitae*), oriental fruit fly (*Dacus(Bactrocera) dorsalis*), rice leafminer (*Agromyza oryzae*), onion maggot (*Delia antiqua*), seedcorn maggot (*Delia platura*), soybean pod gall midge (*Asphondylis* sp.), muscid fly (*Musca domestica*), house mosquito (*Culex pipiens pipiens*), etc.; TYLENCHIDA including coffee root-lesion nematode (*Pratylenchus coffeae*), potato cyst nematode (*Glabodera rostchiensis*), root-knot nematode (*Meloidogyne* sp.), citrus nematode (*Tylenchulus semipenetrans*), *Aphelenchus* sp. (*Aphelenchus avenae*), chrysanthemum foliar (*Aphelenchoides ritzemabosi*), etc.; and ACARINA including citrus red mite (*Panonychus citri*), fruit tree red spider mite (*Panonychus uimi*), carmine spider mite (*Tetranychus cinnabarinus*), Kanzawa spider mite (*Tetranychus KanzawaI Kishida*), two-spotted spider mite (*Tetranychus urticae Koch*), pink tea rust mite (*Acaphylla theae*), pink citrus rust mite (*Aculops pelekassi*), purple tea mice (*Calacarus carinatus*), pear rust mite (*Epitrimerus pyri*), etc.

The agrohorticultural insecticide, which contains as an active ingredient the phthalamide derivative of the general formula (I) of the present invention has a marked insecticidal effect on the above-typical insect pests injurious to paddy field crops, upland crops, fruit trees, vegetables, other crops, flowers and ornamental plants, and the like. Therefore, the desired effect of the agrohorticultural insecticide of the present invention can be obtained by applying the present agrohorticultural insecticide to the nursery facility; paddy field; upland field; seeds or stalks and leaves of fruits, vegetables, other crops, flowers and ornamental plants; cultural medium such as paddy field water, soil, etc.; at a season at which the insect pests are expected to appear, before their appearance or at the time when their appearance is confirmed. Particularly, a preferable application for using the agrohorticultural insecticide of the present invention is the application for which so-called "penetration and translocation" are utilized, wherein the present agrohorticultural insecticide is applied to the nursery soil of crops, flowers and ornamental plants or the like; the picking-in hole soil at a transplantation; the plant roots; the irrigation water; or the cultural water of a water culture; so as to uptake the compound of the present application from the roots through or not through the soil.

The agrohorticultural insecticide of the present invention is generally prepared into conveniently usable forms according to an ordinary manner for preparation of agrochemicals.

That is, the phthalamide derivative represented by the general formula (I) and, optionally, an adjuvant are blended with a suitable inert carrier in a proper proportion and prepared into a suitable preparation form such as a suspension, emulsifiable concentrate, soluble concentrate, wettable powder, granulated wettable powder, granules, dust, tablets, pack or the like through dissolution, dispersion, suspension, mixing, impregnation, adsorption, or sticking.

The inert carrier usable in the present invention may be either solid or liquid. As a material usable as the solid carrier, it includes soybean flour, cereal flour, wood flour, bark flour, saw dust, powdered tobacco stalks, powdered walnut shells, bran, powdered cellulose, extraction residue of vegetables, synthetic polymers such as powdered synthetic resins, clays (e.g. kaolin, bentonite, and acid clay), talcs (e.g. talc and pyrophyllite), silicas (e.g. diatomaceous earth, silica sand, mica, and white carbon [synthetic, high-dispersion silicic acid, also called finely divided hydrated silica or hydrated silicic acid, some of commercially available products contain calcium silicate as the major component]), activated carbon, powdered sulfur, pumice, calcined diatomaceous earth, ground brick, fly ash, sand, calcium carbonate, calcium phosphate and other inorganic or mineral powders, plastic supports such as polyethylene, polypropylene, poly(vinylidene chloride), chemical fertilizers such as ammonium sulfate, ammonium phosphate, ammonium nitrate, urea, and ammonium chloride, and compost. These carriers may be used alone or as a mixture thereof.

A material usable as the liquid carrier is selected from materials that have solubility in themselves or which are without such solubility but are capable of dispersing an active ingredient with the aid of an adjuvant. The following are typical examples of the liquid carrier and can be used alone or as a mixture thereof: water, alcohols (e.g. methanol, ethanol, isopropanol, butanol, and ethylene glycol), ketones (e.g. acetone, methyl ethyl ketone, methyl isobutyl ketone, diisobutyl ketone, and cyclohexanone), ethers (e.g. ethyl ether, dioxane, Cellosolve, dipropyl ether, and tetrahydrofuran), aliphatic hydrocarbon (e.g. kerosene and mineral oils), aromatic hydrocarbons (e.g. benzene, toluene, xylene, solvent naphtha, and alkylnaphthalenes), halogenated hydrocarbons (e.g. dichloroethane, chloroform, carbon tetrachloride, and chlorobenzene), esters (e.g. ethyl acetate, diisopropyl phthalate, dibutyl phthalate, and dioctyl phthalate), amides (e.g. dimethylformamide, diethylformamide, and dimethylacetamide), nitriles (e.g. acetonitrile), and dimethyl sulfoxide.

The following are typical examples of other adjuvants, which are used depending upon purposes and used alone or in combination thereof in some cases, or need not be used at all.

To emulsify, disperse, dissolve and/or wet a compound as active ingredient, a surfactant is used. Examples of the surfactants include polyoxyethylene alkyl ethers, polyoxyethylene alkylaryl ethers, polyoxyethylene higher fatty acid esters, polyoxyethylene resonates, polyoxyethylene sorbitan monolaurate, polyoxyethylene sorbitan monooleate, alkylarylsulfonates, naphthalene sulfonic acid condensation products, ligninsulfonates, and higher alcohol sulfate esters.

Further, to stabilize the dispersion of a compound as active ingredient, tackify it and/or bind it, the adjuvants exemplified below may also be used, namely, there may also be used adjuvants such as casein, gelatin, starch, methyl cellulose, carboxymethyl cellulose, gum arabic, poly(vinyl alcohol)s, turpentine, bran oil, bentonite, and ligninsulfonates.

To improve the flowability of a solid product, the following adjuvants may also be used, namely, there may be used adjuvants such as waxes, stearates, alkyl phosphates, etc.

Adjuvants such as naphthalenesulfonic acid condensation products and polycondensates of phosphates may be used as a peptizer for dispersible products.

Adjuvants such as silicone oils may also be used as a defoaming agent.

Adjuvants such as 1,2-benzisothiazoline-3-one, parachlorometaxylenol, butyl paraoxybenzoate may also be added as a preservative.

Further, if necessary, functional spreading agents, active enhancers such as metabolic decomposition inhibitor like piperonyl butoxide, anti-freezing agents such as propylene glycol, antioxidants such as BHT, ultraviolet absorbers, and the like may also be added.

The content of the compound as active ingredient may be varied as required, and the compound as active ingredient may be used in a proportion properly chosen in the range of 0.01 to 90 parts by weight per 100 parts of the agrohorticultural insecticide. For example, in dusts or granules, the suitable content of the compound as active ingredient is from 0.01 to 50% by weight. In emulsifiable concentrates or wettable powders, it is also from 0.01 to 50% by weight.

The agrohorticultural insecticide of the present invention is used to control a variety of insect pests in the following manner: it is applied to a crop on which the insect pests are expected to appear, or a site where appearance of the insect pests is undesirable, as it is or after being properly diluted with or suspended in water or the like, in an amount effective for control of the insect pests.

The applying dosage of the agrohorticultural insecticide of the present invention is varied depending upon various factors such as a purpose, insect pests to be controlled, a growth state of a plant, tendency of insect pests appearance, weather, environmental conditions, a preparation form, an application method, an application site, and application time. It may be properly chosen in the range of 0.001 g to 10 kg, preferably 0.01 g to 1 kg, (in terms of the compound as active ingredient) per 10 are depending upon purposes.

The agrohorticultural insecticide of the present invention may be used in admixture with other agrohorticultural insecticides, acaricides, nematocides, fungicides, biotic pesticides or the like in order to expand both spectrum of controllable insect pest species and the period of time when effective application are possible or to reduce the dosage. Furthermore, the agrohorticultural insecticide of the present invention may be used in admixture with herbicides, plant growth regulators, fertilizers or the like, depending upon application situations.

As the other agrohorticultural insecticides, acaricides, and nematocides, which are used for the above purpose, there can be exemplified agrohorticultural insecticides, acaricides, and nematocides, such as Ethion, Trichlorfon, Metamidophos, Acephate, Dichlorvos, Mevinphos, Monocrotophos, Malathion, Dimethoate, Formothion, Mecarbam, Vamidothion, Thiometon, Disulfoton, Oxydeprofos, Naled, Methylparathion, Fenitrothion, Cyanophos, Propaphosi Fenthion, Prothiofos, Profenofos, Isofenphos, Temephos, Phenthoate, Dimethylvinphos, Chlorfenvinphos, Tetrachlorvinphos, Phoxim, Isoxathion, Pyraclofos, Methidathion, Chlorpyrifos, Chlorpyrifos-methyl, Pyridaphenthion, Diazinon, Pirimiphosmethyl, Phosalone, Phosmet, Dioxabenzophos, Quinalphos, Terbuphos, Ethoprophos, Cadusafos, Mesulfenfos, DPS (NK-0795), Phosphocarb, Fenamiphos, Isoamidophos, Fosthiazate, Isazophos, Ethoprophos, Fenthion, Fostietane, Dichlofenthion, Thionazin, Sulprofos, Fensulfothion, Diamidafos, Pyrethrin, Allethrin, Prallethrin, Resmethrin, Permethrin, Tefluthrin, Bifenthrin, Fenpropathrin, Cypermethrin, α-Cypermethrin, Cyhalothrin, λ-Cyhalothrin, Deltamethrin, Acrinathrin, Fenvalerate, Esfenvalerate, Flucythrinate, Fluvalinate, Cycloprothrin, Ethofenprox, Halfenprox, Silafluofen, Flucitrinate, Fluvalinate, Methomyl, Oxamyl, Thiodicarb, Aldicarb, Alanycarb, Cartap, Metolcarb, Xylylcarb, Propoxur, Phenoxycarb, Fenobucarb, Ethiophencarb, Fenothiocarb, Bifenazate, BPMC, Carbaryl, Pirimicarb, Carbofuran, Carbosulfan, Furathiocarb, Benfuracarb, Aldoxycarb, Diafenthiuron, Diflubenzuron, Teflubenzuron, Hexaflumuron, Novaluron, Lufenuron, Flufenoxuron, Chlorfluazuron, Fenbutatinoxide, tricyclohexyltinhydroxide, sodium oleate, potassium oleate, Methoprene, Hydroprene, Binapacryl, Amitraz, Dicofol, Kersen, Chrorobenzilate, Phenisobromolate, Tetradifon, Bensultap, Benzomate, Tebufenozide, Methoxyfenozide, Chromafenozide, Propargite, Acequinosyl, Endosulfan, Diofenolan, Chlorfenapyl, Fenpyroximate, Tolfenpyrad, Fipronil, Tebufenpyrad, Triazamate, Etoxazole, Hexythiazox, nicotine sulfate, Nitenpyram, Acetamiprid, Thiacloprid, Imidacloprid, Thiamethoxam, Clothianidin, Dinotefuran, Fluazinam, Pyriproxyfen, Hydramethylnon, Pyrimidifen, Pyridaben, Cyromazin, TPIC (tripropyl isocyanurate), Pymetrozin, Clofentezin, Buprofedin, Thiocyclam, Fenazaquin, Chinomethionate, Indoxacarb, Polynactin complexes, Milbemectin, Abamectin, Emamectin-benzoate, Spinosad, BT (Bacillus thuringiensis), Azadirachtin, Rotenone, hydroxypropyl starch, Levamisole hydrochloride, Metamsodium, Morantel tartrate, Dazomet, Trichlamide, Pasteuria, Monacrosporium-phymatophagum, etc. As the agrohorticultural fungicides used for the same purpose as above, there can be exemplified agrohorticultural fungicides such as sulfur, lime sulfur, copper sulfate basic, Iprobenfos, Edifenfos, Tolclofos-methyl, Thiram, Polycarbamate, Zineb, Manzeb, Mancozeb, Propineb, Thiophanate, Thiophanate methyl, Benomyl, Iminoctadin acetate, Iminocutadin albecylate, Mepronil, Flutolanil, Pencycuron, Furametpyl, Thifluzamide, Metalaxyl, Oxadixyl, Carpropamid, Dichlofluanid, Flusulfamide, Chlorothalonil, Kresoxim-methyl, Fenoxanil (NNF-9425), Himexazol, Eclomezol, Fluoroimide, Procymidone, Vinclozolin, Iprodione, Triadimefon, Triflumizole, Bitertanol, Triflumizole, Ipconazole, Fluconazole, Propiconazole, Diphenoconazole, Myclobutanil, Tetraconazole, Hexaconazole, Tebuconazole, Imibenconazole, Prochloraz, Pefurazoate, Cyproconazole, Isoprothiolane, Fenarimol, Pyrimetanil, Mepanipyrim, Pyrifenox, Fluazinam, Triforine, Diclomezine, Azoxystrobin, Thiadiazin, Captan, Probenazole, Acibenzolar-S-methyl (CGA-245704), Fthalide, Tricyclazole, Pyroquilon, Chinomethionat, Oxolinic acid, Dithianon, Trifloxystrobin, Cyazofamid, Thiadinil, Dichlosimet, Kasugamycin, Validamycin, Polyoxin, Blasticidin, Streptomycin, etc. Similarly, as the herbicides, there can be exemplified herbicides such as Glyphosate, Sulfosate, Glyfosinate, Bialaphos, Butamifos, Esprocarb, Prosulcarb, Benthiocarb, Pyributycarb, Asulam, Linulon, Dymron, Bensulfuron-methyl, Cyclosulfamuron, Cinosulfuron, Pyrazosulfuron ethyl, Azimsulfuron, Imazosulfuron, Tenylchlor, Alachlor, Pretilachlor, Clomeprop, Etobenzanid, Mefenacet, Pendimethalin, Bifenox, Acifluorfen, Lactfen, Cyhalofop-butyl, Ioxynil, Bromobutide, Alloxydim, Setoxydim, Napropamide, Indanofan, Pyrazolate, Benzofenap, Pyraflufen-ethyl, Imazapyl, Sulfentrazone, Cafenstrole, Bentoxazon, Oxadiazon, Paraquat, Diquat, Pyriminobac, Simazine, Atrazine, Dimethametryn, Triazyflam, Benflesate, Flutiacet-methyl, Quizalofop-ethyl, Bentazon, Oxaziclomefone, Azafenidin, Benzobicyclone, calcium peroxide, etc.

As to the biotic pesticides, the same effect as above canbe expected by using the agrohorticultural insecticide of the present invention in admixture with, for example, viral formulations obtained from nuclear polyhedrosis virus (NPV), granulosis virus (GV), cytoplasmic polyhedrosis virus (CPV), entomopox virus (EPV), etc.; microbial pesticides utilized as insecticides or nematicides, such as *Monacrosporium phymatophagum, Steinernema carpocapsae, Steinernema kushidai, Pasteuria penetrans*, etc.; microbial pesticides utilized as fungicides, such as *Trichoderma lignorum, Agrobacterium radiobactor*, nonpathogenic *Erwinia carotovora, Bacillus subtilis*, etc.; and biotic pesticides utilized as herbicides, such as *Xanthomonas campestris*, etc.

In addition, the agrohorticultural insecticide of the present invention can be used in combination with biotic pesticides including natural enemies such as Parasitic wasp (*Encarsia formosa*), Parasitic wasp (*Aphidius colemani*), Gall-mildge (*Aphidoletes aphidimyza*), Parasitic wasp (*Diglyphus isaea*), Parasitic mite (*Dacnusa sibirica*), Predatory mite (*Phytoseiulus persimilis*), Predatory mite (*Amblyseius cucumeris*), Predatory bug (*Orius sauteri*), etc.; microbial pesticides such as *Beauveria brongniartii*, etc.; and pheromones such as (Z)-10-tetradecenyl=acetate, (E,Z)-4,10-tetradecadienyl=acetate, (Z)-8-dodecenyl=acetate, (Z)-11-tetradecenyl=acetate, (Z)-13-icosen-10-one, (Z)-8-dodecenyl=acetate, (Z)-11-tetradecenyl=acetate, (Z)-13-icosen-10-one, 14-methyl-1-octadecene, etc.

Typical formulation examples and test examples of the present invention are described below but they should not be construed as limiting the scope of the invention.

As used in the formulation examples, the terms "part" and "parts" are by weight.

| Formulation Example 1 | |
|---|---|
| Each compound listed in Tables 1 to 3 | 10 parts |
| Xylene | 70 parts |
| N-methylprrolidone | 10 parts |

-continued

| Formulation Example 1 | |
|---|---|
| Mixture of polyoxyethylene nonylphenyl ether and calcium alkylbenzenesulfonate | 10 parts |

An emulsifiable concentrate is prepared by mixing uniformly the above ingredients to effect dissolution.

| Formulation Example 2 | |
|---|---|
| Each compound listed in Tables 1 to 3 | 3 parts |
| Clay powder | 82 parts |
| Diatomaceous earth powder | 15 parts |

A dust is prepared by mixing uniformly and grinding the above ingredients.

| Formulation Example 3 | |
|---|---|
| Each compound listed in Tables 1 to 3 | 5 parts |
| Mixed powder of bentonite and clay | 90 parts |
| Calcium ligninsulfonate | 5 parts |

Granules are prepared by mixing the above ingredients uniformly, and kneading the resulting mixture together with a suitable amount of water, followed by granulation and drying.

| Formulation Example 4 | |
|---|---|
| Each compound listed in Tables 1 to 3 | 20 parts |
| Kaolin and synthetic high-dispersion silicic acid | 75 parts |
| Mixture of polyoxyethylene nonylphenyl ether and calcium alkylbenzenesulfonate | 5 parts |

A wettable powder is prepared by mixing uniformly and grinding the above ingredients.

TEST EXAMPLE 1

Insecticidal Test on Diamond Back Moth (*Plutella xylostella*)

Adult diamond back moths were released and allowed to oviposit on a Chinese cabbage seedling. Two days after the release, the seedling having the eggs deposited thereon was immersed for about 30 seconds in a liquid chemical prepared by diluting a preparation containing each compound listed in Tables 1 to 3 as an active ingredient to adjust the concentration to 50 ppm. After air-dryness, it was allowed to stand in a room thermostatted at 25° C. Six days after the immersion, the hatched insects were counted. The mortality was calculated according to the following equation and the insecticidal effect was judged according to the criterion shown below. The test was carried out with triplicate groups of 10 insects.

$$\text{Corrected mortality (\%)} = \frac{\text{Number of hatched insects in untreated group} - \text{Number of hatched insects in treated group}}{\text{Number of hatched insects in untreated group}} \times 100$$

| Criterion: |
|---|
| A --- Mortality 100% |
| B --- Mortality 99–90% |
| C --- Mortality 89–80% |
| D --- Mortality 79–50% |
| E --- Mortality 49% or less |

The result is shown in Table 4 below.

TEST EXAMPLE 2

Insecticidal Test on Common Cutworm (*Spodoptera litura*)

A piece of cabbage leaf (cultivar; Shikidori) was immersed for about 30 seconds in a liquid chemical prepared by diluting a preparation containing each compound listed in Tables 1 to 3 as an active ingredient to adjust the concentration to 50 ppm. After air-dryness, it was placed in a plastic Petri dish with a diameter of 9 cm and inoculated with second-instar larvae of common cutworm, after which the dish was closed and then allowed to stand in a room thermostatted at 25° C. Eight days after the inoculation, the dead and alive were counted. The mortality was calculated according to the following equation and the insecticidal effect was judged according to the criterion shown in Test Example 1. The test was carried out with triplicate groups of 10 insects.

$$\text{Corrected mortality (\%)} = \frac{\text{Number of alive larvae in untreated group} - \text{Number of alive larvae in treated group}}{\text{Number of alive larvae in treated group}} \times 100$$

The result is shown in Table 4 below.

TEST EXAMPLE 3

Insecticidal Test on Smaller Tea Tortrix (*Adoxophyes* sp.)

Tea leaves were immersed for about 30 seconds in a liquid chemical prepared by diluting a preparation containing each compound listed in Tables 1 to 3 as an active ingredient to adjust the concentration to 50 ppm. After air-dryness, the tea leaves were placed in a plastic Petri dish with a diameter of 9 cm and inoculated with larvae of smaller tea tortrix, after which the dish was allowed to stand in a room thermostatted at 25° C. and having a humidity of 70%. Eight days after the inoculation, the dead and alive larvae were counted and, the mortality was calculated according to the equation shown in Test Example 2, and the insecticidal effect was judged according to the criterion shown in Test Example 1. The test was carried out with triplicate groups of 10 insects.

The result is shown in Table 4 below.

TABLE 4

| No. | Test Example 1 | Test Example 2 | Test Example 3 |
|---|---|---|---|
| 1-290 | A | A | A |
| 1-292 | A | A | A |
| 1-296 | A | A | A |
| 1-297 | A | A | A |
| 1-298 | A | A | A |
| 1-372 | A | A | A |
| 1-374 | A | A | A |
| 1-458 | A | A | A |
| 1-459 | A | A | A |
| 1-460 | A | A | A |
| 2-22 | A | A | A |
| 2-23 | A | A | E |
| 2-24 | A | A | A |
| 3-5 | A | E | A |
| 3-6 | A | D | E |
| 3-7 | A | A | A |
| 3-24 | A | A | A |
| 3-26 | A | A | A |

The invention claimed is:

1. A phthalamide derivative of formula (I):

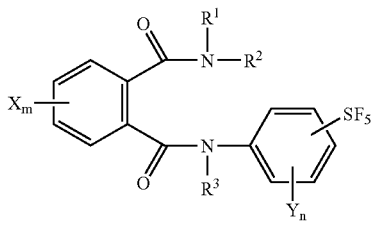

wherein
$R^1$ represents hydrogen; $C_{3-6}$ cycloalkyl; halo $C_{3-6}$ cycloalkyl; phenyl; substituted phenyl having one or more substituents, which may be the same or different, selected from the group consisting of halogen, $C_{1-6}$ alkyl, halo $C_{1-6}$ alkyl, $C_{1-6}$ alkoxy, halo $C_{1-6}$ alkoxy, $C_{1-6}$ alkylthio, halo $C_{1-6}$ alkylthio, $C_{1-6}$ alkylsulfinyl, halo $C_{1-6}$ alkylsulfinyl, $C_{1-6}$ alkylsulfonyl, and halo $C_{1-6}$ alkylsulfonyl; heterocyclyl; substituted heterocyclyl having one or more substituents, which may be the same or different, selected from the group consisting of halogen, $C_{1-6}$ alkyl, halo $C_{1-6}$ alkyl, $C_{1-6}$ alkoxy, halo $C_{1-6}$ alkoxy, $C_{1-6}$ alkylthio, halo $C_{1-6}$ alkylthio, $C_{1-6}$ alkylsulfinyl, halo $C_{1-6}$ alkylsulfinyl, $C_{1-6}$ alkylsulfonyl, and halo $C_{1-6}$ alkylsulfonyl; or the group -A-(G)$_r$,
$R^2$ and $R^3$, which may be the same or different, represent hydrogen, $C_{1-6}$ alkyl, halo $C_{1-6}$ alkyl, $C_{3-6}$ alkenyl, halo $C_{3-6}$ alkenyl, $C_{3-6}$ alkynyl, halo $C_{3-6}$ alkynyl, $C_{3-6}$ cycloalkyl, halo $C_{3-6}$ cycloalkyl, $C_{1-6}$ alkoxy $C_{1-6}$ alkyl, $C_{1-6}$ alkylthio $C_{1-6}$ alkyl, formyl, $C_{1-6}$ alkylcarbonyl, halo $C_{1-6}$ alkylcarbonyl, $C_{1-6}$ alkoxycarbonyl, mono $C_{1-6}$ alkylaminocarbonyl, or same or different di $C_{1-6}$ alkylaminocarbonyl; or $R^2$ together with A, $R^1$, G, $R^4$, or $R^6$ optionally forms a 4- to 8-membered ring that is optionally interrupted with 1 or 2 oxygen, sulfur, or nitrogen, which may be the same or different;
each X, which may be the same or different, represents halogen, nitro, cyano, $C_{1-6}$ alkyl, halo $C_{1-6}$ alkyl, $C_{2-6}$ alkenyl, halo $C_{2-6}$ alkenyl, $C_{2-6}$ alkynyl, halo $C_{2-6}$ alkynyl, $C_{1-6}$ alkoxy, halo $C_{1-6}$ alkoxy, $C_{1-6}$ alkylcarbonyloxy, halo $C_{1-6}$ alkylcarbonyloxy, $C_{1-6}$ alkylsulfonyloxy, halo $C_{1-6}$ alkylsulfonyloxy, $C_{1-6}$ alkylthio, halo $C_{1-6}$ alkylthio, $C_{1-6}$ alkylsulfinyl, halo $C_{1-6}$ alkylsulfinyl, $C_{1-6}$ alkylsulfonyl, or halo $C_{1-6}$ alkylsulfonyl; or two groups X that are adjacent to each other on an aromatic ring optionally together form a fused ring, which optionally has one or more substituents, which may be the same or different, selected from the group consisting of halogen, cyano, nitro, $C_{1-6}$ alkyl, halo $C_{1-6}$ alkyl, $C_{1-6}$ alkoxy, halo $C_{1-6}$ alkoxy, $C_{1-6}$ alkylthio, halo $C_{1-6}$ alkylthio, $C_{1-6}$ alkylsulfinyl, halo $C_{1-6}$ alkylsulfinyl, $C_{1-6}$ alkylsulfonyl, and halo $C_{1-6}$ alkylsulfonyl;

m represents an integer of 0 to 2;

each Y, which may be the same or different, represents halogen; nitro; cyano; $C_{1-6}$ alkyl; halo $C_{1-6}$ alkyl; cyclo $C_{3-6}$ alkyl; $C_{1-6}$ alkoxy; halo $C_{1-6}$ alkoxy; mono $C_{1-6}$ alkylamino; same or different di $C_{1-6}$ alkylamino; $C_{1-6}$ alkylthio; halo $C_{1-6}$ alkylthio; $C_{1-6}$ alkylsulfinyl; halo $C_{1-6}$ alkylsulfinyl; $C_{1-6}$ alkylsulfonyl; halo $C_{1-6}$ alkylsulfonyl; phenyl; substituted phenyl having one or more substituents, which may be the same or different, selected from the group consisting of halogen, $C_{1-6}$ alkyl, halo $C_{1-6}$ alkyl, $C_{1-6}$ alkoxy, halo $C_{1-6}$ alkoxy, $C_{1-6}$ alkylthio, halo $C_{1-6}$ alkylthio, $C_{1-6}$ alkylsulfinyl, halo $C_{1-6}$ alkylsulfinyl, $C_{1-6}$ alkylsulfonyl, and halo $C_{1-6}$ alkylsulfonyl; phenyl $C_{1-4}$ alkyl; substituted phenyl $C_{1-4}$ alkyl having on a ring one or more substituents, which may be the same or different, selected from the group consisting of halogen, $C_{1-6}$ alkyl, halo $C_{1-6}$ alkyl, $C_{1-6}$ alkoxy, halo $C_{1-6}$ alkoxy, $C_{1-6}$ alkylthio, halo $C_{1-6}$ alkylthio, $C_{1-6}$ alkylsulfinyl, halo $C_{1-6}$ alkylsulfinyl, $C_{1-6}$ alkylsulfonyl, and halo $C_{1-6}$ alkylsulfonyl; phenoxy; substituted phenoxy having one or more substituents, which may be the same or different, selected from the group consisting of halogen, $C_{1-6}$ alkyl, halo $C_{1-6}$ alkyl, $C_{1-6}$ alkoxy, halo $C_{1-6}$ alkoxy, $C_{1-6}$ alkylthio, halo $C_{1-6}$ alkylthio, $C_{1-6}$ alkylsulfinyl, halo $C_{1-6}$ alkylsulfinyl, $C_{1-6}$ alkylsulfonyl, and halo $C_{1-6}$ alkylsulfonyl; phenylthio; substituted phenylthio having one or more substituents, which may be the same or different, selected from the group consisting of halogen, $C_{1-6}$ alkyl, halo $C_{1-6}$ alkyl, $C_{1-6}$ alkoxy, halo $C_{1-6}$ alkoxy, $C_{1-6}$ alkylthio, halo $C_{1-6}$ alkylthio, $C_{1-6}$ alkylsulfinyl, halo $C_{1-6}$ alkylsulfinyl, $C_{1-6}$ alkylsulfonyl, and halo $C_{1-6}$ alkylsulfonyl; heterocyclyl; or substituted heterocyclyl having one or more substituents, which may be the same or different, selected from the group consisting of halogen, cyano, nitro, $C_{1-6}$ alkyl, halo $C_{1-6}$ alkyl, $C_{1-6}$ alkoxy, halo $C_{1-6}$ alkoxy, $C_{1-6}$ alkylthio, halo $C_{1-6}$ alkylthio, $C_{1-6}$ alkylsulfinyl, halo $C_{1-6}$ alkylsulfinyl, $C_{1-6}$ alkylsulfonyl, and halo $C_{1-6}$ alkylsulfonyl; and two groups Y adjacent to each other on an aromatic ring may together form a fused ring, which optionally has one or more substituents, which may be the same or different, and selected from the group consisting of halogen, $C_{1-6}$ alkyl, halo $C_{1-6}$ alkyl, $C_{1-6}$ alkoxy, halo $C_{1-6}$ alkoxy, $C_{1-6}$ alkylthio, halo $C_{1-6}$ alkylthio, $C_{16}$ alkylsulfinyl, halo $C_{1-6}$ alkylsulfinyl, $C_{1-6}$ alkylsulfonyl, or halo $C_{1-6}$ alkylsulfonyl; or Y together with $R^3$ optionally forms a 5- to 7-membered ring that may be interrupted with 1 or 2 oxygen, sulfur, or nitrogen, which may be the same or different;

n represents an integer of 0 to 3,

A represents $C_{1-8}$ alkylene, $C_{3-6}$ alkenylene, or $C_{3-6}$ alkynylene;

each G, which may be the same or different, represents hydrogen; halogen; cyano; nitro; halo $C_{1-6}$ alkyl; $C_{3-6}$ cycloalkyl; halo $C_{3-6}$ cycloalkyl; same or different di $C_{1-6}$ alkoxyphosphoryl; same or different di $C_{1-6}$ alkoxythiophosphoryl; diphenylphosphino; diphenylphosphono; same or different $C_{1-6}$ dialkylsulfonium; phenyl; substituted phenyl having one or more substituents, which may be the same or different, selected from the group consisting of halogen, $C_{1-6}$ alkyl, halo $C_{1-6}$ alkyl, $C_{1-6}$ alkoxy, halo $C_{1-6}$ alkoxy, $C_{1-6}$ alkylthio, halo $C_{1-6}$ alkylthio, $C_{1-6}$ alkylsulfinyl, halo $C_{1-6}$ alkylsulfinyl, $C_{1-6}$ alkylsulfonyl, and halo $C_{1-6}$ alkylsulfonyl; heterocyclyl; substituted heterocyclyl having one or more substituents, which may be the same or different, selected from the group consisting of halogen, $C_{1-6}$ alkyl, halo $C_{1-6}$ alkyl, $C_{1-6}$ alkoxy, halo $C_{1-6}$ alkoxy, $C_{1-6}$ alkylthio, halo $C_{1-6}$ alkylthio, $C_{1-6}$ alkylsulfinyl, halo $C_{1-6}$ alkylsulfinyl, $C_{1-6}$ alkylsulfonyl, and halo $C_{1-6}$ alkylsulfonyl; or the group -Z-$R^4$, r represents an integer of 1 to 3, Z represents —O— or —N($R^5$)—

$R^5$ represents hydrogen; $C_{1-6}$ alkylcarbonyl; halo $C_{1-6}$ alkylcarbonyl; $C_{1-6}$ alkoxycarbonyl; phenylcarbonyl; substituted phenylcarbonyl having one or more substituents, which may be the same or different, selected from the group consisting of halogen, $C_{1-6}$ alkyl, halo $C_{1-6}$ alkyl, $C_{1-6}$ alkoxy, halo $C_{1-6}$ alkoxy, $C_{1-6}$ alkylthio, halo $C_{1-6}$ alkylthio, $C_{1-6}$ alkylsulfinyl, halo $C_{1-6}$ alkylsulfinyl, $C_{1-6}$ alkylsulfonyl, or halo $C_{1-6}$ alkylsulfonyl; $C_{1-6}$ alkylsulfonyl; and halo $C_{1-6}$ alkylsulfonyl;

$R^4$ represents hydrogen; $C_{1-6}$ alkyl; halo $C_{1-6}$ alkyl; $C_{3-6}$ alkenyl; halo $C_{3-6}$ alkenyl; $C_{3-6}$ alkynyl; halo $C_{3-6}$ alkynyl; $C_{3-6}$ cycloalkyl; halo $C_{3-6}$ cycloalkyl; $C_{1-6}$ $C_{1-6}$ alkyl; $C_{1-6}$ alkylthio $C_{1-6}$ alkyl; formyl; $C_{1-6}$ alkylcarbonyl; halo $C_{1-6}$ alkylcarbonyl; $C_{1-6}$ alkoxycarbonyl; mono $C_{1-6}$ alkylaminocarbonyl; same or different di $C_{1-6}$ alkylaminocarbonyl; mono $C_{1-6}$ alkylaminothiocarbonyl; same or different di $C_{1-6}$ alkylaminothiocarbonyl; same or different di $C_{1-6}$ alkoxyphosphoryl; same or different di $C_{1-6}$ alkoxythiophosphoryl; phenyl; substituted phenyl having one or more substituents, which may be the same or different, and selected from halogen, $C_{1-6}$ alkyl, halo $C_{1-6}$ alkyl, $C_{1-6}$ alkoxy, halo $C_{1-6}$ alkoxy, $C_{1-6}$ alkylthio, halo $C_{1-6}$ alkylthio, $C_{1-6}$ alkylsulfinyl, halo $C_{1-6}$ alkylsulfinyl, $C_{1-6}$ alkylsulfonyl, or halo $C_{1-6}$ alkylsulfonyl; phenyl $C_{1-4}$ alkyl; substituted phenyl $C_{1-4}$ alkyl having on a ring one or more substituents, which may be the same or different, and selected from halogen, $C_{1-6}$ alkyl, halo $C_{1-6}$ alkyl, $C_{1-6}$ alkoxy, halo $C_{1-6}$ alkoxy, $C_{1-6}$ alkylthio, halo $C_{1-6}$ alkylthio, $C_{1-6}$ alkylsulfinyl, halo $C_{1-6}$ alkylsulfinyl, $C_{1-6}$ alkylsulfonyl, or halo $C_{1-6}$ alkylsulfonyl; heterocyclyl; or substituted heterocyclyl having one or more substituents, which may be the same or different, selected from halogen, $C_{1-6}$ alkyl, halo $C_{1-6}$ alkyl, $C_{1-6}$ alkoxy, halo $C_{1-6}$ alkoxy, $C_{1-6}$ alkylthio, halo $C_{1-6}$ alkylthio, $C_{1-6}$ alkylsulfinyl, halo $C_{1-6}$ alkylsulfinyl, $C_{1-6}$ alkylsulfonyl, and halo $C_{1-6}$ alkylsulfonyl; or the group —W—$R^6$, W represents —S—, —SO—, —$SO_2$—, —C(=O)—, —C(=S)—, or the group —C(=NOR$^7$)—

$R^7$ represents hydrogen; $C_{1-6}$ alkyl; halo $C_{1-6}$ alkyl; $C_{3-6}$ alkenyl; halo $C_{3-6}$ alkenyl; $C_{3-6}$ alkynyl; $C_{3-6}$ cycloalkyl; phenyl $C_{1-4}$ alkyl; or substituted phenyl $C_{1-4}$ alkyl having on a ring one or more substituents, which may be the same or different, and selected from halogen, $C_{1-6}$ alkyl, halo $C_{1-6}$ alkyl, $C_{1-6}$ alkoxy, halo $C_{1-6}$ alkoxy, $C_{1-6}$ alkylthio, halo $C_{1-6}$ alkylthio, $C_{1-6}$ alkylsulfinyl, halo $C_{1-6}$ alkylsulfinyl, $C_{1-6}$ alkylsulfonyl, or halo $C_{1-6}$ alkylsulfonyl, and $R^6$ represents hydrogen; $C_{1-6}$ alkyl; halo $C_{1-6}$ alkyl; $C_{3-6}$ alkenyl; halo $C_{3-6}$ alkenyl; $C_{3-6}$ alkynyl; halo $C_{3-6}$ alkynyl; $C_{3-6}$ cycloalkyl; halo $C_{3-6}$ cycloalkyl; $C_{1-6}$ alkoxy $C_{1-6}$ alkyl; $C_{1-6}$ alkylthio $C_{1-6}$ alkyl; $C_{1-6}$ alkoxy; halo $C_{1-6}$ alkoxy; $C_{1-6}$ alkylthio; halo $C_{1-6}$ alkylthio; amino; mono $C_{1-6}$ alkylamino; same or different di $C_{1-6}$ alkylamino; $C_{1-6}$ alkoxy $C_{1-6}$ alkylamino; $C_{1-6}$ alkylthio $C_{1-6}$ alkylamino; phenyl; substituted phenyl having one or more substituents, which may be the same or different, and selected from halogen, $C_{1-6}$ alkyl, halo $C_{1-6}$ alkyl, $C_{1-6}$ alkoxy, halo $C_{1-6}$ alkoxy, $C_{1-6}$ alkylthio, halo $C_{1-6}$ alkylthio, $C_{1-6}$ alkylsulfinyl, halo $C_{1-6}$ alkylsulfinyl, $C_{1-6}$ alkylsulfonyl, or halo $C_{1-6}$ alkylsulfonyl; phenyl $C_{1-4}$ alkyl; substituted phenyl $C_{1-4}$ alkyl having on a ring one or more substituents, which may be the same or different, and selected from halogen, $C_{1-6}$ alkyl, halo $C_{1-6}$ alkyl, $C_{1-6}$ alkoxy, halo $C_{1-6}$ alkoxy, $C_{1-6}$ alkylthio, halo $C_{1-6}$ alkylthio, $C_{1-6}$ alkylsulfinyl, halo $C_{1-6}$ alkylsulfinyl, $C_{1-6}$ alkylsulfonyl, or halo $C_{1-6}$ alkylsulfonyl; phenylamino; substituted phenylamino having on a ring one or more substituents, which may be the same or different, selected from the group consisting of halogen, $C_{1-6}$ alkyl, halo $C_{1-6}$ alkyl, $C_{1-6}$ alkoxy, halo $C_{1-6}$ alkoxy, $C_{1-6}$ alkylthio, halo $C_{1-6}$ alkylthio, $C_{1-6}$ alkylsulfinyl, halo $C_{1-6}$ alkylsulfinyl, $C_{1-6}$ alkylsulfonyl, or halo $C_{1-6}$ alkylsulfonyl; phenyl $C_{1-4}$ alkylamino; substituted phenyl $C_{1-4}$ alkylamino having on a ring one or more substituents, which may be the same or different, and selected from halogen, $C_{1-6}$ alkyl, halo $C_{1-6}$ alkyl, $C_{1-6}$ alkoxy, halo $C_{1-6}$ alkoxy, $C_{1-6}$ alkylthio, halo $C_{1-6}$ alkylthio, $C_{1-6}$ alkylsulfinyl, halo $C_{1-6}$ alkylsulfinyl, $C_{1-6}$ alkylsulfonyl, or halo $C_{1-6}$ alkylsulfonyl; heterocyclyl; substituted heterocyclyl having one or more substituents, which may be the same or different, and selected from halogen, $C_{1-6}$ alkyl, halo $C_{1-6}$ alkyl, $C_{1-6}$ alkoxy, halo $C_{1-6}$ alkoxy, $C_{1-6}$ alkylthio, halo $C_{1-6}$ alkylthio, $C_{1-6}$ alkylsulfinyl, halo $C_{1-6}$ alkylsulfinyl, $C_{1-6}$ alkylsulfonyl, or halo $C_{1-6}$ alkylsulfonyl; heterocyclic amino; or substituted heterocyclic amino having on a ring one or more substituents, which may be the same or different, and selected from halogen, $C_{1-6}$ alkyl, halo $C_{1-6}$ alkyl, $C_{1-6}$ alkoxy, halo $C_{1-6}$ alkoxy, $C_{1-6}$ alkylthio, halo $C_{1-6}$ alkylthio, $C_{1-6}$ alkylsulfinyl, halo $C_{1-6}$ alkylsulfinyl, $C_{1-6}$ alkylsulfonyl, or halo $C_{1-6}$ alkylsulfonyl; or $R^4$ or $R^6$ together with A optionally form a 4- to 8-membered ring that may be interrupted with 1 or 2 oxygen, sulfur, or nitrogen, which may be the same or different.

2. A phthalamide derivative according to claim 1 wherein $R^1$ represents $C_{1-6}$ alkyl, $C_{1-6}$ alkylthio $C_{1-6}$ alkyl, $C_{1-6}$ alkylsulfinyl $C_{1-6}$ alkyl, or $C_{1-6}$ alkylsulfonyl $C_{1-6}$ alkyl;

$R^2$ and $R^3$ represent hydrogen;

X represents halogen;

m represents 1;

Y represents halogen or $C_{1-6}$ alkyl; and n represents an integer of 0 to 2.

3. An agrohorticultural insecticide comprising one or more phthalamide derivatives according to claim 1 as an active ingredient and one or more inert carriers and optionally one or more adjuvants.

4. A method for using an agrohorticultural insecticide to protect a useful plant from insect pests comprising applying an effective amount of a agrohorticultural insecticide according to claim 3 to a crop plant or to the soil.

* * * * *